(12) United States Patent
Nadal Ginard

(10) Patent No.: US 8,846,099 B2
(45) Date of Patent: *Sep. 30, 2014

(54) PARENTERAL COMPOSITION COMPRISING MICROSPHERES WITH A DIAMETER BETWEEN 10 AND 20 MICRONS

(71) Applicant: Coretherapix, SLU, Madrid (ES)

(72) Inventor: Bernardo Nadal Ginard, Madrid (ES)

(73) Assignee: Coretherapix, SLU, Tres Cantos (ES)

( * ) Notice: Subject to any disclaimer, the term of this patent is extended or adjusted under 35 U.S.C. 154(b) by 0 days.

This patent is subject to a terminal disclaimer.

(21) Appl. No.: 13/873,812

(22) Filed: Apr. 30, 2013

(65) Prior Publication Data

US 2013/0315997 A1    Nov. 28, 2013

Related U.S. Application Data

(63) Continuation of application No. 13/573,720, filed on Oct. 3, 2012, now abandoned, and a continuation of application No. 13/425,044, filed on Mar. 20, 2012, now abandoned, and a continuation of application No. 13/217,569, filed on Aug. 25, 2011, now abandoned, and a continuation of application No. 13/057,764, filed as application No. PCT/EP2009/060171 on Aug. 5, 2009, now abandoned.

(30) Foreign Application Priority Data

Aug. 5, 2008 (GB) .................................. 0814302.6

(51) Int. Cl.
| | | |
|---|---|---|
| A61K 9/14 | (2006.01) | |
| A61K 9/51 | (2006.01) | |
| A61K 38/18 | (2006.01) | |
| A61K 38/30 | (2006.01) | |
| A61K 9/50 | (2006.01) | |
| A61K 9/00 | (2006.01) | |
| A61K 9/16 | (2006.01) | |

(52) U.S. Cl.
CPC ............. *A61K 9/0019* (2013.01); *A61K 9/5031* (2013.01); *A61K 38/30* (2013.01); *A61K 38/1833* (2013.01); *A61K 38/18* (2013.01); *A61K 9/1605* (2013.01)
USPC ............... 424/489; 514/7.6; 514/8.5; 514/9.5

(58) Field of Classification Search
None
See application file for complete search history.

(56) References Cited

U.S. PATENT DOCUMENTS

| | | | |
|---|---|---|---|
| 6,007,845 A | 12/1999 | Domb et al. | |
| 6,261,585 B1 | 7/2001 | Sefton et al. | |
| 6,451,303 B1 | 9/2002 | Whitehouse et al. | |
| 2002/0013273 A1 | 1/2002 | Shirley et al. | |
| 2003/0054973 A1 | 3/2003 | Anversa | |
| 2005/0170005 A1 | 8/2005 | Rashba-Step et al. | |
| 2006/0134070 A1 | 6/2006 | Mandrusov et al. | |
| 2007/0053870 A1 | 3/2007 | Tae et al. | |
| 2007/0098736 A1 | 5/2007 | Cleland et al. | |
| 2007/0122487 A1 | 5/2007 | DeLuca et al. | |
| 2009/0297621 A1* | 12/2009 | Lim et al. ..................... 424/501 |
| 2013/0189321 A1 | 7/2013 | Nadal-Ginard | |

FOREIGN PATENT DOCUMENTS

| | | |
|---|---|---|
| EP | 1295596 | 3/2003 |
| EP | 1350518 A1 | 10/2003 |
| EP | 1987817 | 7/2009 |
| EP | 2087890 | 8/2009 |
| JP | 2005104910 | 4/2005 |
| KR | 8017161 A | 2/2008 |
| WO | 9618388 | 6/1996 |
| WO | 9847532 | 10/1998 |
| WO | 9908728 | 2/1999 |
| WO | 9924061 | 5/1999 |
| WO | 0028969 | 5/2000 |
| WO | 03103611 | 12/2003 |
| WO | 2004022000 A2 | 3/2004 |
| WO | 2005007122 A2 | 1/2005 |
| WO | 2005055949 | 6/2005 |
| WO | 2006117422 | 11/2006 |
| WO | 2007028053 | 3/2007 |
| WO | 2007055561 A1 | 5/2007 |
| WO | 2007059010 | 5/2007 |
| WO | 2008108736 | 9/2008 |
| WO | 2009097349 | 8/2009 |
| WO | 2009100128 | 8/2009 |

OTHER PUBLICATIONS

K Matsumoto, T Nakamura. "Renotropic role and therapeutic potential of HGF in the kidney." Nephrology Dialysis Transplatation, vol. 17 Suppl 9, pp. 59-61.*

J Morrissey, K Hruska, G Guo, S Wang, Q Chen, S Klahr. "Bone Morphogenetic Protein-7 Improves Renal Fibrosis and Accelerates the Return of Renal Function." Journal of the American Society of Nephrology, vol. 13, 2002, pp. S14-S24.*

(Continued)

*Primary Examiner* — Frederick Krass
*Assistant Examiner* — Isaac Shomer
(74) *Attorney, Agent, or Firm* — Klauber & Jackson LLC

(57) ABSTRACT

The present invention relates to pharmaceutical formulations suitable for targeting particular tissue and/or organ(s) with a formulated active ingredient, for example when administered upstream of the target organ or tissue, and to use of the same in treatment, methods of treatment administering the same and methods of preparing the formulations. The pharmaceutical formulations of the invention are for parenteral administration to a target tissue and comprise particles containing an active ingredient, and a biodegradable excipient, wherein 90% or more of the particles have a diameter of between 10 and 20 microns and the formulation is substantially free of particles with a diameter greater than 50 microns and less than 5 microns, such that where the formulation is administered upstream of the target tissue the ability of the active to pass through the target tissue and pass into systemic circulation is restricted.

21 Claims, 14 Drawing Sheets

(56) References Cited

OTHER PUBLICATIONS

G Stokman, JC Leemans, N Classen, JJ Weening, S Florquin. Hematopoietic Stem Cell Mobilization Therapy Accelerates Recovery of Renal Function Independent of Stem Cell Contribution. Journal of the American Society of Nephrology, vol. 16, 2005, pp. 1684-1694.*

K Matsumoto, T Nakamura. "Renotropic role and therapeutic potential of HGF in the kidney." Nephrology Dialysis Transplantation. vol. 17 Supplement 9, 2002, pp. 59-61.*

Hatzistergos, et al., "Randomised comparison of growth hormone versus IGF-1 on early post-myocardial infarction ventricular remodelling in rats", Growth Hormone and IGF Research, Churchill Livingstone, London, GB, vol. 18, No. 2, pp. 157-165, Feb. 28, 2008.

Maulik, et al., "Growth factor/s and cell therapy in myocardial regeneration", Journal of Molecular and Celluar Cardiology, Academic Press, GB, vol. 44, No. 2, pp. 219-227, Jan. 22, 2008.

Sakaguchi G., et al., "Control-Released Hepatocyte Growth Factor Prevents the Progression of Heart Failure in Stroke-Prone Spontaneously Hypertensive Rats", The Annals of Thoracic Surgery, Elsevier LNKD, vol. 79, No. 5., pp. 1627-1634, May 1, 2005.

Arras, et al., "The Delivery of Angiogenic Factors to the Heart by Microsphere Therapy," Nature Biotechnology, vol. 16, Feb. 1998, pp. 159-162.

Bowen, P., "Particle Size Distribution Measurement from Millimeters to Nanometers and from Rods to Platelets," Journal of Dispersion Science and Technology, vol. 23, No. 5, 2002, pp. 631-662, Marcel Dekker, In., 270 Madison Avenue, New York, NY, 10016, US.

Hosaka, et al., "Gelatin Hydrogel Microspheres Enable Pinpoint Delivery of Basic Fibroblast Growth Factor for the Development of Functional Collateral Vessels," Circulation, 2004; 110: pp. 3322-3328.

Poe, N.D., "The Effects of Coronary Arterial Injection of Radioalbumin Macroaggregates on Coronary Hemodynamics and Myocardial Function," Journal of Nuclear Medicine, vol. 12, No. 11, (1971) pp. 724-731.

Anversa, et al., Nature, "Myocyte renewal and ventricular remodelling," 2002; 415: 240.

Nadal-Ginard, et al., Circ. Res., "Myocyte death, growth, and regeneration in cardiac hypertrophy and failure," 2003; 92: 139.

Kocher, et al., Nature Med., "Neovascularization of ischemic myocardium by human bone-marrow-derived angioblasts . . . ," 2001; 7: 430.

Menasche, et al., Lancet, "Myoblast transplantation for heart failure," 2001; 357: 279.

Guo, et al., The Journal of Thoracic and Cariovasc Surgery, "Myoblast-based cardiac repair: Xenomyoblast vs. allomyoblast transplantation," 2007; 134: 1332.

Wagers, et al., Cell, "Plasticity of adult stem cells," 2004; 116: 636-648.

Balsam, et al., Nature, "Haematopoietic stem cells adopt mature haematopoietic fates in ischaemic myocardium," 2004; 428: 668-673.

Murry, et al., Nature, "Haematopoietic stem cells do not transdifferentiate into cardiac myocytes in myocardiual infacts," 2004; 428: 664-668.

Chien, Nature, "Stem cells: lost in translation," 2004; 428: 607-608.

Rangappa, et al., Ann Thorac Surg, "Transformation of adult mesenchymal stem cells isolated from the fatty tissue into cardiomyocytes," 2003; 75: 775.

Asahara, et al., Circ Res., "Bone marrow origin of endothelial progenitor cells responsible for postnatal vasculogenesis . . . ," 1999; 85: 221-228.

Orlic, et al., Nature, "Bone marrow cells regenerate infracted myocardium," 2001; 410: 701.

Orlic, et al., PNAS USA, "Mobilized bone marrow cells repair the infracted heart, improving function and survival," 2001; 98: 10344.

Tse, et al., Lancet, "Angiogenesis in ischaemic myocardium by intramyocardial autologous bone marrow mononuclear cell implantation," 2003; 361: 47.

Perin, et al., Circulation, "Transendocardial, autologous bone marrow cell transplantation for severe, chronic ischemic heart failure," 2003; 107: 2294.

Quaini, et al., New Eng J of Medicine, "Chimerism of the transplanted heart," 2002; 346: 5.

Bayes-Genis, et al., Cardiovasc. Res., "Host cell-derived cariomyocytes in sex-mismatch cardiac allografts," 2002; 56: 404.

Bayes-Genis, et al., Eur J Heart Fail., "Cardiac chimerism in receipients of peripheral-blood and bone marrow stem cells," 2004; 6: 399.

Thiele, et al., Transplantation, "Mixed chimerism of cardiomyocytes and vessels after allongeneic bone marrow and stem-cell transplantation . . . ," 2004; 77: 1902.

Nadal-Ginard, et al., J Clin Invest, "A matter of life and death: cardiac myocyte apoptosis and regeneration," 2003, 111: 1427.

Beltrami, et al., Cell, "Adult cardiac stem cells are multipotent and support myocardial regeneration," 2003; 114: 763-776.

Torella, et al., Circ. Res., "Cardiac stem cell and myocyte aging, heart failure, and insulin-like growth factor-1 overexpression," 2004; 94: 514.

Mendez-Ferrer, et al., Nature Clin Prac Cardiovasc Med., "Resident progenitors and bone marrow stem cells . . . ," 2006; 3(1): S83.

Torella, et al., Cell Mol Life Sci., "Resident cardiac stem cells," 2007; 64: 661.

Beltrami, et al., N Engl J Med., "Evidence that human cardiac myocytes divide after myocardial infarction," 2001; 344: 1750.

Urbanek, et al., PNAS USA, "Intense myocyte formation from cardiac stem cells in human cardiac hypertrophy," 2003; 100: 10440.

Anvrsa, et al., N Engl J Med., "Chimerism of the transplanted heart," 2002; 346: 1410.

Ellison, et al., J Biol. Chem., "Acute beta-adrenergic overload produces myocyte damage through calcium leakage . . . ," 2007; 282: 11397-11409.

Haider, et al., J Mol Med., "Angiomyogenesis for cardiac repair using human myoblasts as carriers of human vascular . . . ," 2004; 82: 539.

Folkman, et al., Cell, "Blood vessel formation: what is its molecular basis?", 1996; 87: 1153.

Isner, et al., Nature Medicine, "Therapeutic angiogenesis for heart failure," 1999; 5: 491.

Yamaguchi, et al., Circulation, "Stromal cell-derived factor-1 effects on ex vivo expanded endothelial progenitor cell . . . ," 2003; 107: 1322.

Henry, et al., Circulation, "The VIVA trial: Vascular endothelial growth factor in Ischemia for vascular angiogenesis," 2003; 107: 1359.

Laugwitz, et al., Nature, "Postnatal isl1+ cardioblasts enter fuly differentiated cardiomyocyte lineages," 2005; 433: 647-653.

Torella, et al., Rev Exp Cardiol, "Cardiovascular regenerative medicine at the crossroads. Clinical trials of cellular therapy . . . ," 2006; 59: 1175-89.

Oh, et al., PNAS USA, "Cardiac progenitor cells from adult myocardium: homing, differentiation, and fusion after infarction," 2003; 100(21): 12313-8.

Matsuura, et al., J Biol. Chem., "Adult cardiac Sca-1-positive cells differentiate into beating cardiomyocytes," 2004; 279(12): 11384-11391.

Wang et al., "Preparation technologies of monodisperse polymer microspheres", Material Engineering, 2004, 11, 61-64, Abstract only.

Tian et al., "Preparation of uniform size PLGA microparticles and microcapsules by premix membrane emulsification", Chinese Journal of Engineering, Aug. 31, 2009, 4, 754-762, Abstract only.

Fu et al., "Methods of preparation of uniform-sized and monodisperse drug-loaded microspheres and their applications", Chinese Journal of Pharmaceuticals, 2011, 42, 856-870, Abstract only.

Igaku no Ayumi, "Hematopoietic cytokine for regeneration therapy of ischemic heart disease", Progress in Medicine, 2006, 217, 409-413, Abstract.

McGee et al., "Zero order release of protein from poly(D,L-lactide-co-glycolide microparticles prepared using a modified phase separation technique", Journal of Controlled Release, 1995, 34, 77-86.

Miksa et al., "Polypyrrole core/polyacrolein shell latex for protein immobilization", Colloid and Polymer Science, 1995, 273, 47-52.

(56) References Cited

OTHER PUBLICATIONS

Crotts et al., "Preparation of porous and nonporous biodegradable polymeric hollow microspheres", Journal of Controlled Release, 1995, 35, 91-105.
Page et al., "Myocardial changes associated with cardiogenic shock", New Engl J Med, 1971, 285, 133-137.
Pfeffer et al., "Ventricular remodeling after myocardial infarction, Experimental observations and clinical implications", Circulation, 1990, 81, 1161-1172.
Takahashi et al., "Induction of pluripotent stem cells from adult human fibroblasts by defined factors", Cell, 2007, 131, 861-872.
MacLellan et al, "Genetic dissection of cardiac growth control pathways", Annu Rev Physiol, 2000, 62, 289-319.
Reinlib et al., "Cell transplantation as future therapy for cardiovascular disease? A workshop of the National Heart, Lung, and Blood Institute", Circulation, 2000, 101, e182-e187.
Pasumarthi et al., "Cardiomyocyte cell cycle regulation", Circ Res, 2002, 90, 1044-1054.
MacLellan, "Mending broken hearts one cell a a time", J Mol Cell Cardiol, 2002, 34, 87-89.
Murry et al., "Haematopoietic stem cells do not transdifferentiate into cardiac myocytes in myocardial infarcts", Nature, 2004, 428, 664-668.
Haider et al., "Angiomyogenesis for cardiac repair using human myoblasts as carriers of human vascular endothelial growth factor", Journal of Molecular Medicine, 2004, 82, 539-549.
Lee et al., "Interleukin-13 induces tissue fibrosis by selectively stimulating and activating transforming growth factor beta1", J Exp Med, 2001, 194, 809-821.
Gandia et al., "Human dental pulp stem cells improve left ventricular function, induce angiogenesis, and reduce infarct size in rats with acute myocardial infarction", Stem Cells, 2008, 26, 638-645.
Behfar et al., "Cardiopoietic programming of embryonic stem cells for tumor-free heart repair", J Exp Med, 2007, 204, 405-420.
Sijbesma et al., "Reversible polymers formed from self-complementary monomers using quadruple hydrogen bonding", Science, 1997, 278, 1601-1604.
Dankers et al., "A modular and supramolecular approach to bioactive scaffolds for tissue engineering", Nature Materials, 2005, 4, 568-574.
Ellison et al., "Endogenous cardiac stem cell activation by insulin-like growth factor-1/hepatocyte growth factor intracoronary injection fosters survival and regeneration of the infarcted pig heart", Journal of the American College of Cardiology, 2011, 58, 977-986.
Bergmann et al., "Evidence for cardiomyocyte renewal in humans", Science, 2009, 324, 98-102.
Laflamme et al., "Heart regeneration", Nature, 2011, 473, 326-335.
Hsieh et al., "Evidence from a genetic fate-mapping study that stem cells refresh adult mammalian cardiomyocytes after injury", Nature Medicine, 2007, 13, 970-974.
Senyo et al., "Mammalian heart renewal by pre-existing cardiomyocytes", Nature, 2013, 493, 433-436.
Malliaras et al., "Cardiomyocyte proliferation and progenitor cell recruitment underlie therapeutic regeneration after myocardial infarction in the adult mouse heart", EMBO Mol Med, 2013, 5, 191-209.
Bersell et al., "Neuregulin1/ErbB4 signaling induces cardiomyocyte proliferation and repair of heart injury", Cell, 2009, 138, 257-270.
Goumans et al., "TGF-beta1 induces efficient differentiation of human cardiomyocyte progenitor cells into functional cardiomyocytes in vitro", Stem Cell Research, 2008, 1, 138-149.
Urbanek et al., "Myocardial regeneration by activation of multipotent cardiac stem cells in ischemic heart failure", Proceedings of the National Academy of Sciences of the United States of America, 2005, 102, 8692-8697.
Doetsch, "A niche for adult neural stem cells", Curr Opin Genet Dev, 2003, 13, 543-550.
Doetsch et al, "Subventricular zone astrocytes are neural stem cells in the adult mammalian brain", Cell, 1999, 97, 703-716.
Kuang et al., "Asymmetric self-renewal and commitment of satellite stem cells in muscle", Cell, 2007, 129, 999-1010.
Collins et al., "Stem cell function, self-renewal, and behavioral heterogeneity of cells from the adult muscle satellite cell niche", Cell, 2005, 122, 289-301.
Noseda et al., "Cardiopoietic factors: extracellular signals for cardiac lineage commitment", Circ Res, 2011, 108, 129-152.
Linke et al., "Stem cells in the dog heart are self-renewing, clonogenic, and multipotent and regenerate infarcted myocardium, improving cardiac function", Proceedings of the National Academy of Sciences of the United States, 2005, 102, 8966-8971.
Hahn et al., "Pre-treatment of mesenchymal stem cells with a combination of growth factors enhances gap junction formation, cytoprotective effect on cardiomyocytes, and therapeutic efficacy for myocardial infarction", J Am Coll Cardiol, 2008, 51, 933-943.
Takehara et al., "Controlled delivery of basic fibroblast growth factor promotes human cardiosphere-derived cell engraftment to enhance cardiac repair for chronic myocardial infarction", J Am Coll Cardiol, 2008, 52, 1858-1865.
Roggia et al., "Hepatocyte growth factor (HGF) enhances cardiac commitment of differentiating embryonic stem cells by activating PI3 kinase", Experimental Cell Research, 2007, 313, 921-930.
Chimenti et al., "Relative roles of direct regeneration versus paracrine effects of human cardiosphere-derived cells transplanted into infarcted mice", Circulation Research, 2010, 106, 971-980.
Ruvinov et al., "The promotion of myocardial repair by the sequential delivery of IGF-1 and HGF from an injectable alginate biomaterial in a model of acute myocardial infarction", Biomaterials, 2011, 32, 565-578.
Nadal-Ginard, "Cardiovascular regenerative medicine at the crossroads. Clinical trials of cellular therapy must now be based on reliable experimental data from animals with characteristics similar to human's", Rev Esp Cardiol, 2006, 59, 1175-1189.
Urbanek et al., "Cardiac stem cells possess growth factor-receptor systems that after activation regenerate the infarcted myocardium, improving ventricular function and long-term survival", Circulation Research, 2005, 97, 663-673.
Sansdrap et al., "Influence of manufacturing parameters on the size characteristics and the release profiles of nifedipine from poly(DL-lactide-co-glycolide) microspheres", International Journal of Pharmaceutics, 1993, 98, 157-164.
Office Action dated Mar. 11, 2013 for U.S. Appl. No. 13/425,041.
Office Action dated Aug. 9, 2013 for U.S. Appl. No. 13/425,041.
Office Action dated Sep. 6, 2013 for Australian Patent Application No. 2009279086.
Berkland et al, "Fabrication of PLG microspheres with precisely controlled and monodisperse size distributions", Journal of Controlled Release, 2001, 73, 59-74.
Jiang et al., "IGF-I synergizes with FGF-2 to stimulate oligodendrocyte progenitor entry into the cell cycle", Developmental Biology, 2001, 232, 414-423.

* cited by examiner

| Qd (mL/h) | Qt (mL/min) | dp (micras) | CV (%) | DS (micras) |
|---|---|---|---|---|
| 3,5 | 3 | 15,0 | 7,32 | 1,09 |

FIGURE 11A
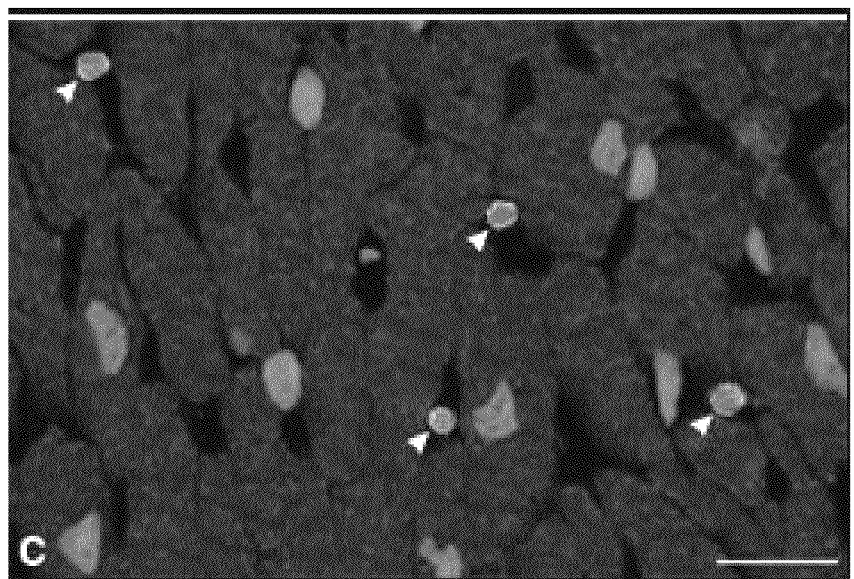
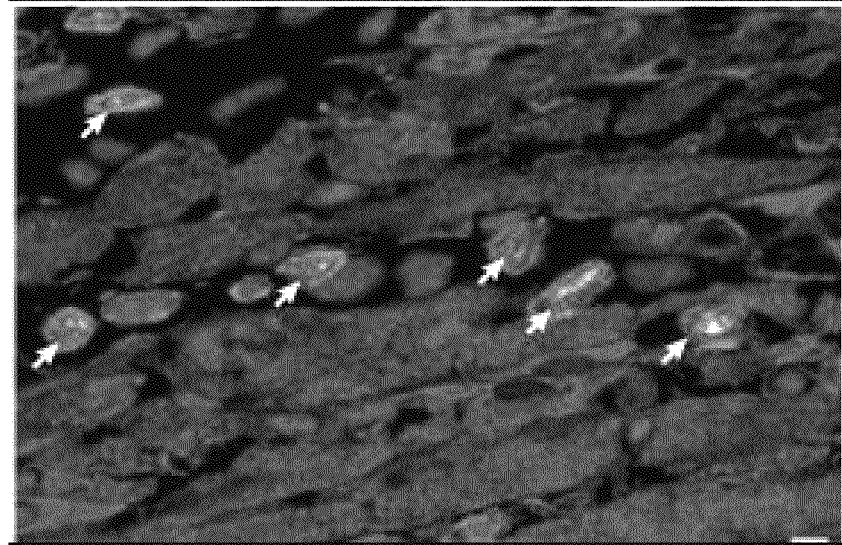
FIGURE 11B

PARENTERAL COMPOSITION COMPRISING MICROSPHERES WITH A DIAMETER BETWEEN 10 AND 20 MICRONS

CROSS REFERENCE TO RELATED APPLICATIONS

The present application is a Continuation of co-pending non-provisional application Ser. No. 13/573,720, filed Oct. 3, 2012, which is a Continuation of application Ser. No. 13/425,044, filed Mar. 20, 2012, which is a Continuation of application Ser. No. 13/217,569, filed Aug. 25, 2011, which, in turn, is a Continuation of non-provisional application Ser. No. 13/057,764, filed Feb. 6, 2011, which, in turn, claims the priority of PCT Application No. PCT/EP2009/060171 filed Aug. 5, 2009, which in turn, claims priority from Great Britain application Serial No. 0814302.6 filed Aug. 5, 2008. Applicant claims the benefits of 35 U.S.C. §120 as to the non-provisional and PCT applications, and priority under 35 U.S.C. §119 as to the said Great Britain application, and the entire disclosures of all applications are incorporated herein by reference in their entireties.

FIELD OF THE INVENTION

The present disclosure relates to pharmaceutical formulations suitable for targeting particular tissue and/or organ(s) with a formulated active ingredient, for example when administered upstream of the target organ or tissue. The disclosure also relates to use of the same in treatment, methods of treatment administering the same and methods of preparing the formulations.

In particular different growth factors and cytokines are employed to stimulate the intrinsic regenerative capacity of solid tissues by activating its resident stem cell population using a device, such as a catheter, for the localized delivery of the active compounds to the target tissue.

BACKGROUND OF THE INVENTION

Most medicines/pharmaceuticals are administered systemically, for example orally, intravenously, by vaccine, intramuscularly or the like. Notable exceptions are stents coated with active ingredients, certain respiratory formulations delivered directly to the lungs, certain radiotherapies which are directed to target areas and certain dermatological, ophthalmological, and otological treatments which are administered topically.

Nevertheless, when appropriate, it would be advantageous to be able to deliver the pharmaceutical primarily to a diseased tissue or organ, because this would reduce the dose required and also minimize side effects. Such an approach would be particularly advantageous for two main areas of medicine: a) the administration of growth factors and cytokines capable of activating the growth and differentiation of resident stem cells in a particular tissue. Because of the potent biological activity of these molecules, it would be desirable to limit their action to the intended tissue, with minimal or no spillover to the rest of the body; b) the delivery of cancer chemotherapeutic agents because if the cancerous tissue could be targeted specifically then it may allow the administration of higher doses to the targeted cells while minimizing the terrible toxic side effects of the same, at least to a significant extent.

In more acute situations such as in heart attacks and strokes better treatments may be possible, particularly those directed to regenerate the damaged tissue, if the organs affected could be specifically targeted. In chronic situations, such as Parkinson disease, diabetes, or pulmonary fibrosis, local administration of agents capable to reconstitute the deficient cell type(s) have the potential to improve the prognosis of the disease.

However, reproducible delivery of active ingredients to target tissue or a target organ in a therapeutically effective manner is influenced to a large extent on the components (including excipients) employed, their physical characteristics, the dose and the mode of delivery.

BRIEF DESCRIPTION OF THE DRAWINGS

FIGS. 1A and 1B are micrographs, and FIG. 1C-1E are or include graphs.

FIGS. 2A, 2B-2D and 2F are micrographs, and FIGS. 2C, 2G and 2H are graphs.

FIGS. 3A-3E and 3G are micrographs, and FIGS. 3F, 3H and 3I are graphs.

FIGS. 4A-4C, 4E, 4F, 4H and 4I are micrographs, and FIGS. 4D and 4G are graphs.

FIGS. 5A-5F and 5I are micrographs, and FIGS. 5G and 5H are graphs.

FIGS. 6A-6E are micrographs, FIGS. 6F-6H are graphs, and FIG. 6I is a series of graphs with micrograph inserts.

FIGS. 11A and 11B are micrographs and show sections of porcine heart wherein endogenous cardiac stem cells are highlighted.

Figures 1A, 1B, 1C, 1D, 1E:
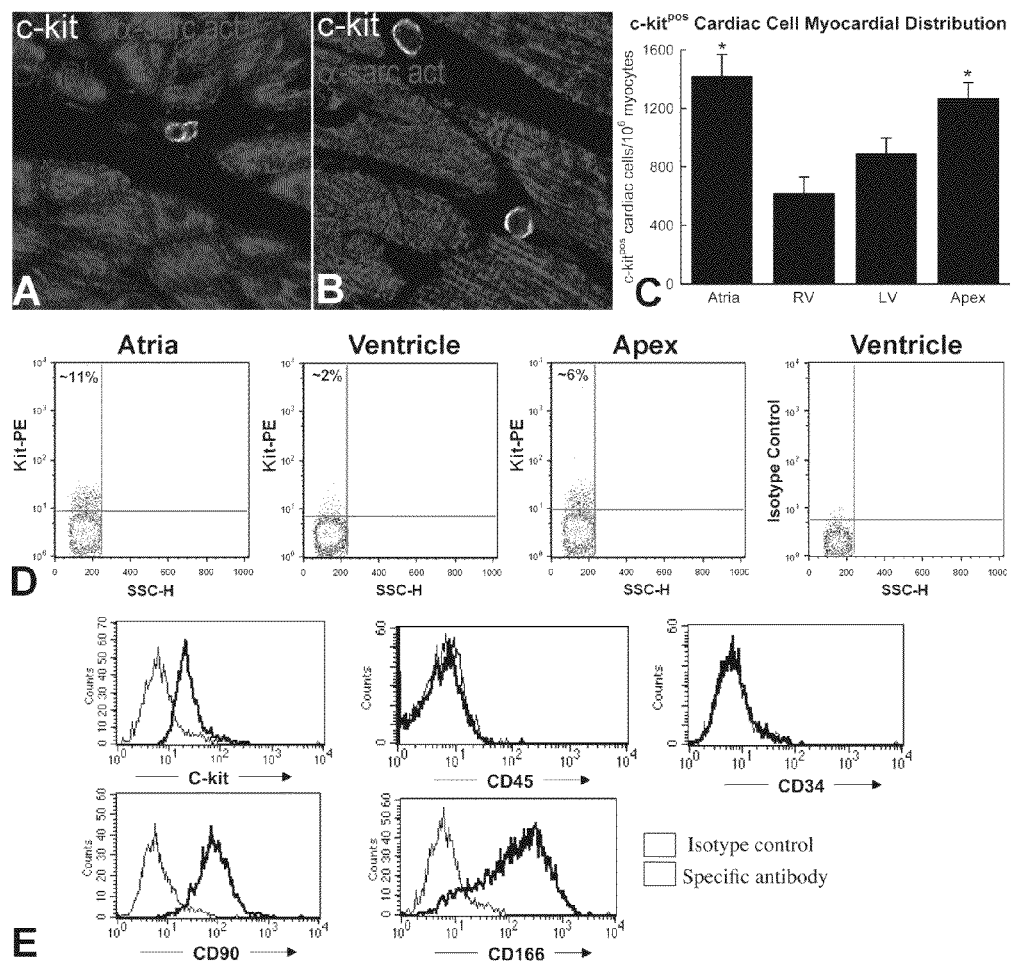
FIGS. 1A-1E show distribution and characterization of c-kite$^{pos}$ cardiac cells in the adult porcine heart.

The present disclosure provides a pharmaceutical formulation for parenteral, especially intra-arterial, administration to a target tissue comprising particles containing an active ingredient and a biodegradable polymer excipient, wherein 30% or more of the particles have a diameter of 25 microns or less and the formulation is substantially free of particles with a diameter greater than 50 microns, such that where the formulation is administered upstream of the target tissue the ability of the active ingredient to pass through the target tissue and pass into systemic circulation is restricted. That is to say the active ingredient is retained in the target tissue while its ability to pass through the target tissue and pass into systemic circulation is severely restricted or abolished. Thus, in a particular aspect of the invention a pharmaceutical formulation for parenteral administration to a cardiac tissue is provided, said pharmaceutical composition comprising particles containing an active ingredient and a biodegradable excipient, wherein 90% or more of the particles have a diameter of between 10 and 20 microns and the formulation is substantially free of particles with a diameter greater than 50 microns and less than 5 microns, such that where the formulation is administered upstream of the target tissue the ability of the active to pass through the target tissue and pass into systemic circulation is restricted. In one embodiment at least 90%, of the particles of the pharmaceutical invention have a diameter that is between 15 and 20 microns.

In an aspect of the invention a pharmaceutical formulation for parenteral, e.g. intra-arterial, administration to a cardiac tissue is provided, said pharmaceutical composition comprising particles containing an active ingredient, selected from the group consisting of HGF and IGF-1, and a biodegradable excipient, wherein 90% or more of the particles have a diameter of between 10 and 20 microns and the formulation is substantially free of particles with a diameter greater than 50 microns and less than 5 microns, such that where the formulation is administered upstream of the cardiac tissue the ability of the active to pass through the cardiac tissue and pass into systemic circulation is restricted.

Whilst not wishing to be bound by theory it is thought that formulations of the present disclosure, when administered in the arterial blood upstream of the target tissue or organ, are carried into the target tissue or organ by the circulation and due to the particle size and distribution lodge, in other words are trapped or caught in the capillaries in the tissue or organ, which are about 5-10 μm in diameter. Particles lodging in capillaries and blocking blood flow is not generally desirable but the number of capillaries affected by the formulation of the disclosure is relatively small, particularly as the formulation enables very low therapeutic doses to be employed. Furthermore, the biodegradable excipient melts, dissolves, degrades or in some way disassociates itself from the active and thus ultimately the "blockage" is removed. Thus the movement of the particle is restricted/retarded by lodging in capillaries, a reversible process which returns the capillaries back to the natural condition after a short period. Retarding the movement of the particle for a short period allows the active to be maintained in the vicinity of the target for an appropriate amount of time to facilitate local action or absorption of the active into the extravascular space of the tissue.

The formulation is designed such that most, if not all the active is released from the particle while immobilized in the target tissue vascular bed. Once the active load is released the particle is designed to be degraded and its constituent materials released into the general circulation to be either metabolized or eliminated through the liver and/or kidney.

The present disclosure provides a pharmaceutical formulation for parenteral administration to a target tissues comprising particles containing an active ingredient and a biodegradable excipient, wherein 30% or more of the particles have a diameter of 25 microns or less and the formulation is substantially free of particles with a diameter greater than 50 microns, such that where the formulation is administered upstream of the target tissue the active is retained in the target tissue or organ for a therapeutically effective period.

In particular the formulations of the present disclosure allow lower quantities of active ingredients to be employed because the majority of active is retained in the target tissue rather than being taken into the systemic circulation. This seems to increase the therapeutic window of the active. That is to say the dose range over which the ingredient is therapeutically active is increased allowing smaller absolute quantities to be administered. Local administration of a lower dose means that side effects are likely to be minimised.

Suitable doses are, for example in the range 0.05 μg/Kg to about 10 μg/Kg, such as 0.1 μg/Kg to about 0.5 μg/Kg, in particular 0.15, 0.2, 0.25, 0.35, 0.4 or 0.45 μg/Kg.

Administrating lower doses locally for therapeutic effect is particularly important for potent molecules, for example growth factors, which are known to have potential to stimulate oncogenesis. These potentially harmful side effects limit the utility of such molecules even though in the right circumstance they produce therapeutically beneficial effects.

The formulations of the present disclosure do not employ microspheres comprising a polystyrene, silica or other non-biodegradable bead with active ingredient attached thereto, because enduring resilient materials i.e. non-biodegradable materials such as polystyrene and silica may cause damage to local capillaries, and may act as foreign bodies and produce local inflammatory reactions. Moreover, such non-biodegradable beads might eventually gain access to the systemic circulation and may then, for example accumulate in distant tissue such as the lungs and liver, all of which are undesirable.

Generally, each particle will comprise active and excipient. It is not intended that the description of the formulation refer to discrete particles of active and separate particles of biodegradable polymer in simple admixture.

Substantially free of particles over 50 microns as employed supra is intended to refer to formulations that meet the criteria to be administered as a parenteral formulation set down in the US pharmacopeia and/or European pharmacopeia.

In one embodiment substantially free may include containing less than 5% of said particles, particularly less than 1%, for example less than 0.5%, such as less than 0.1%.

In one embodiment the at least 50%, at least 60%, at least 70%, at least 75%, at least 80%, at least 85%, at least 90%, at least 95%, at least 98% such as at least 99% of the particles have a diameter of 25 microns or less.

In one embodiment the particle size is in the range 6 to 25 microns, such as 10 to 20 microns, particularly 15 or 20 microns, for example at least 50%, at least 60%, at least 70%, at least 75%, at least 80%, at least 85%, at least 90%, at least 95%, at least 98% such as at least 99% of the particles are the relevant size or within said range. Thus in one embodiment of the invention at least 95%, at least 98% or at least 99% of the particles of the pharmaceutical composition have a diameter of between 10 and 20 microns. In another embodiment at least 95%, at least 98% or at least 99% of the particles of the pharmaceutical composition have a diameter of between 15 and 20 microns.

In one embodiment the formulation does not contain particles less than 1 micron in diameter.

In one embodiment the formulation does not contain particles less than 5 microns in diameter.

In one embodiment at least 30% of the particles with the active are retained in the target tissue after administration, for example at least 40%, at least 50%, at least 60%, at least 70%, such as at least 80% or more of the active particles are retained.

In one embodiment the active particle is retained in the target tissue or organ for a period in the range 5 minutes to 24 hours, for example 30 minutes to 5 hours, such as 1, 2, 3 or 4 hours.

The period that the formulation is retained in the relevant tissue or organ depends primarily on the excipient or the combination of excipients employed. Thus the properties required from the excipient in vivo are that:

it is biocompatible (i.e. generally non-toxic and suitable for administration to humans and/or animals), within an appropriate time frame after administration it contributes to maintaining the particle integrity sufficiently for the particle movement to be retarded by, for example lodging in a capillary or arteriole in the target tissue or organ, and it is biodegradable (that is to say it is capable of being processed or metabolised) by the body to release the active and after the active has been released.

Thus a biodegradable polymer excipient suitable for use in the present disclosure is a polymer or co-polymer that does not have a long residency time in vivo, ie would not include entities such a polystyrene, polypropylene, high density polyethene and material with similar properties. Biodegradable polymers must be non-toxic and broken down into non-toxic sub-units preferably locally, such that the amount of circulating fragments/debris from the excipient are minimised.

Suitable excipients can be found in the United States Pharmacopeia (USP) and include inorganic as well organic, natural and man-made polymers. Examples may include polymers such as polylactic acid, polygycolide or a combination of the same namely polylactic co-glycolic acid, polycaprolactone (which has a slower rate of biodegradation than polylactic co-glycolic acid), polyhydroxybutyrate or combinations thereof. Polyurethanes, polysaccharides, proteins and polyaminoacids, carbohydrates, kitosane, heparin, polyhyaluronic acid, etc may also be suitableThe excipient is generally in the form of a particle, an approximate sphere (microsphere) to which the active can be attached or with which the active is associated or incorporated within.

Liposomes are not biodegradable polymer excipients within the meaning of the present disclosure. Liposomes are vesicles of a phospholipid bilayer generally comprising cholesterol. For diseases such as myocardical infarction induced by arterio sclerosis cholesterol levels are monitored as one of the risk factors for the disease and thus it may be advisable to avoid administering cholesterol containing formulations to such patients. In addition patients with liver cirrhosis may have increased difficulty metabolising lipids and dietary fats, therefore administration of liposomes to such patients may not be advisable.

In one embodiment the biodegradable excipient is not a hydrogel (a continuous phase of a corresponding colloidal dispersed phase).

Thus, both the rate of "release" of the active and the rate of "dissolution" of the particle can be altered by altering the excipient or/and the method of binding the active to the excipient, so for example employing polycaprolactone would provide a particle which takes longer to dissolve or disintegrate than a corresponding particle employing polylactic co-glycolic acid. If the active is embedded within the excipient it will be released more slowly than if it is on the surface of the particle. If on the surface and bound by electrostatic charge it will be released faster than if covalently bound.

In one embodiment the excipient comprises polylactic co-glycolic acid.

In one embodiment substantially all the particles, for example 80, 85, 90, 95, 96, 97, 98, 99 or 100% of the particles comprise polylactic co-glycolic acid.

In one embodiment the polylactic co-glycolic acid is in the ratio 75:25 respectively.

In one embodiment the excipient comprises two or more distinct polymers, the term polymer includes co-polymers.

In one embodiment the excipient may include an acrylate polymer, for example a methacrylate polymer.

In one embodiment the particle comprises alginate.

In one embodiment the excipient comprises a biodegradable form of polyurethane.

In one embodiment the excipient is in the form of a microsphere.

In one embodiment the disclosure employs a polyvinyl alcohol microsphere formulation.

In one embodiment the microspheres are not albumin.

In one embodiment the active(s) employed are encapsulated within a biodegradable coating for example selected from the Eudragit range.

In one embodiment one or more active molecules are embedded within the particle.

For the active compounds to perform, as described in the present disclosure, they need to be administered into the circulation as a microparticle which because of its size, morphology and composition will travel with the blood flow to reach its target tissue. At the target, the particle should release its active load in a controllable manner. To accomplish this goal, once unloaded, the particle should be degraded and its constituents either metabolized or delivered into the systemic circulation to be eliminated by the normal excretion systems of the body.

To accomplish these goals the microparticles should fulfill the following characteristics:

The microparticles should be of uniform size and morphology in order to insure that they reach and become lodged at the designed level of the circulatory system. Uniformity of size and shape is better controlled when the particles are spherical.

Most capillary beds allow free passage of particles with a diameter of <6 microns in diameter, the microspheres of this disclosure should have a diameter >6 microns, and preferably of ~15 microns. Particles in the range of 20 microns in diameter or larger lodge into pre-capillary arterioles or arterioles and block the blood flow to several capillaries at once. Therefore, they might create microscopic infarctions. Thus for the delivery of regenerative therapies the most suitable diameter of the microspheres is in the range of 15 microns. In addition, however, particles having diameters of 5, 6, 7, 8, 9, 10, 11, 12, 13, 14, 16, 17, 18, 19, 20, 21, 22, 23, 24 and 25 are contemplated for use according to the present invention.

The time required to release the active compound once they have reached their target could range from minutes to days and even weeks, depending on the type of microsphere and the therapeutic goal.

The microspheres should be made with a biodegradable and non-toxic compound. The stability of the particle and its degradation time will depend on the composition and type of the microsphere. It might be designed to deliver its load before it starts degrading; alternatively it might be designed so that the delivery of its load occurs as the particle disintegrates.

The nature of the polymer used as excipient, its size, lability of the bonds between the monomers and degree of cross-linking, if any, will affect the rate of release of the active as well as the stability and degradability of the particle.

In all embodiments, the microspheres should be stable enough in solution for them not to substantially break or degrade during their administration into the circulation and the time required for them to reach the target vascular bed.

In a suitable embodiment of the disclosure, each particle will carry a single type of active compound. When a mixture of compounds is thought to be beneficial for therapeutic purposes, a mixture of microparticles, each loaded with a single type of compound, may be administered. This design simplifies the production of the therapeutic compounds and offers greater therapeutic flexibility, thereby allowing individualized medicaments to be prepared rapidly to meet the patient's individual specific needs.

In one embodiment a particle(s) employed has/have only one type of active molecule bound to it/them.

In one embodiment a particle(s) employed has a mixture, such as two, three or four active molecules bound to it.

The active compound might be loaded onto the particle at the time of its formation and, for example be dispersed throughout the particle.

The active compound may be encapsulated inside the particle where the excipient forms the shell of the microsphere.

In one embodiment active(s) are bound to a particle(s) by covalent bonds, for example a polypeptide or protein is bonded to a microsphere through cross-linking by treatment with an aldehyde such as formaldehyde or glutaldehyde, for example by emulsifying the microsphere (or ingredient of the microspheres) in the presence of the active(s), a suitable aldehyde and homogenizing the mixture under conditions suitable for forming particles of the required size. Alternatively the active may be bonded to a carboxylate group located on the excipient microsphere.

In one embodiment the active(s) are bound to a particle(s) by electrostatic forces (charge).

In one embodiment the active(s) are bound to a particle(s) through a polyelectrolyte such as, for example comprising sodium, potassium, magnesium and or calcium ions with chloride counter ions in aqueous solution.

In one embodiment the active(s) are bound to a particle(s) between layers of polyelectrolytes.

The active compound may be loaded on the surface of the particle either by charge (electrostatic forces) or covalently bound. In one embodiment the active(s) is/are bound to the particle by electrostatic charge.

In one embodiment the active(s) is/are bound to the particle by polyelectolytes, for example by means of a polyelectrolyte shell covering the particle onto which the active attaches by charge.

The active compound may form a single layer on the surface of the particle or might be deposited in multiple layers either contiguous or separated by polyelectrolyte layers.

The active compound may be bound to the particle by means of "linkers" which on one hand bind to the excipient matrix and on the other to the active compound. These bonds might be either electrostatic or covalent.

The microparticles may for example be stabilized by lyophilization. Microparticle may also be stable when frozen.

In one embodiment the excipient is degraded rapidly in the range of minutes to hours, or over a longer period such as weeks to months.

In one embodiment the formulation is such that once in the circulation one or more actives is/are rapidly released for example in period in the range of 1 to 30 minutes to about 1 to 12 hours.

In one embodiment the disclosure relates to a mixed population of particles that is to say, particles with different rates of "dissolution", which may be used to provide a formulation with controlled or pulsed release.

Thus formulations of the disclosure can comprise particles with different release kinetics and degradation rates.

In one embodiment the active is released over a period of 1 to 24 hours.

In one embodiment the active is released over a period of 1 day to 7 days.

Thus in one or more embodiments all the formulation of the disclosure is metabolized within 7 days of administration.

In one embodiment once in the circulation of the individual, the active(s) is/are released very slowly, over a period weeks to months, for example 1 week to 1, 2, or 3 months.

In one embodiment the population of particles is well characterized and for example has the same characteristics. That is to say the physical and/or chemical properties of each particle fall with a narrow defined range.

In one embodiment the size of the microspheres is monodispersed.

Thus in one embodiment the particles of the formulation have mean particle size with a small standard deviation, for example at least 68% of particles have a size+/−1 micron of the mean, such as 99% of particles have a particle size+/−1 micron of the mean (eg 15+/−1 microns). In addition, compositions wherein the particles have at least 70%, at least 75%, at least 80%, at least 85%, at least 90%, at least 95%, at least 96%, at least 97%, or at least 98% of particles within +/−1 micron of the mean are contemplated by the present invention.

In one embodiment the formulation comprises a population of particles characterized in that the populations contains at least two distinct types of particle, for example the distinct particles may have different actives, coatings, particle size or a combination of the same.

In one embodiment the disclosure relates to a mixed population of particles comprising particles of active in admixture with particles of one or more further distinct actives.

It appears the particle size and distribution of the formulation influences the in vivo profile of the formulation including how the formulation in distributed in the tissue. It seems that is insufficient to simply have a mean particle size within the range 10 to 20 microns because this allows some particles to have a much larger particle size and also a much smaller particle size. This variation can cause problems in vivo because, for example the small particles are not retained with the relevant tissue and the larger particles can damage the tissue.

The amount of active:excipient employed may be in the ratio 1%:99% w/w, 5%:95% w/w, 10%:90% w/w, 20%:80% w/w, 30%:70% w/w, 40%:60% w/w, 50%:50% w/w, 60%:40% w/w, 70%:30% w/w, 80%:20% w/w or 90%:10% w/w, depending on what release profile is required. If the active is required to be release quickly or immediately in vivo a higher ratio of active to excipient may be chosen.

In one embodiment the microsphere employed has a half life of about 16 hours.

In one embodiment the formulation is lyophilized.

In another embodiment the formulation is frozen.

The particles of the disclosure are not magnetic to an appreciable extent.

The active ingredient may be any medicine or pharmaceutical that may be administered in the form of a particle according to the disclosure.

In one embodiment $15 \times 10^6$ particles (microspheres) are administered, such as $14 \times 10^6$, $13 \times 10^6$, $12 \times 10^6$, $11 \times 10^6$, $10 \times 10^6$, $9 \times 10^6$, $8 \times 10^6$, $7 \times 10^6$, $6 \times 10^6$, $5 \times 10^6$, $4 \times 10^6$, $3 \times 10^6$, $2 \times 10^6$ or $1 \times 10^6$ particles are administered.

A particle as employed herein may comprise, for example micronized drug, semi-solid or hydrated entities such as proteins or biologically derived actives formulated as discrete particles provided the particle maintains its structure for a sufficient period to perform the required function. The disclosure also extends to particles with a liquid core provided that the external integrity of the particle is such that is can perform its function in vivo. The disclosure does not extend to particles with a gas core.

Microspheres may be fabricated by emulsifying a polymer solution, followed by evaporation of solvent. In other instances monomers are emulsified followed by thermal or UV polymerization. Alternatively, a polymer melt is emulsified and successively cooled to solidify the droplets. A size reduction of the emulsion can be obtained by homogenizing or sonicating the bulk. The microspheres can be collected by filtering and/or centrifuging the reaction mixture.

Biodegradable microspheres and microcapsules of biopolymers for the controlled release and targeted delivery of different pharmaceutical compounds and therapeutic macromolecules have been long known in a number of forms, particularly those of relatively large diameters as described in the present disclosure (see D. D. Lewis "Biodegradable polymers and drug delivery systems" M. Chasin and R. Langer, editors (Marcel Dekker, New York, 1990); J. P. McGee et al., J. Control. Release 34:77, 1995).

Microspheres and microcapsules are routinely produced by mechanical-physical methods such as spraying constituent monomers into microdroplets of the size followed by either a drying or polymerization step. Such microparticles can also be formed through emulsification followed by removal of the emulsifying solvent (B. Miksa et al., Colloid Polym. Sci. 273: 47, 1995; G. Crotts et al., J. Control. Release 35:91, 1995). The main challenge of these methods is the production of a monodisperse population of particles in shape and size. This, for example can be achieved employing a technique of flow focusing in which a capillary nebulizer is used to form microdroplets of the proper size. In the process the components are submerged into a harvesting solution/solvent which serves to dissolve/suspend the microparticle components, followed by evaporation of the solvent to provide solidified microparticles.

This process may require that all the components of the microparticle be combined into a single mixture (the focused compound) from which are generated the microdroplets that will form the microparticles. As many of the polymers used for drug delivery are hydrophobic while most therapeutic macromolecules, and particularly proteins, are hydrophilic the mixture requires emulsifying to ensure a homogeneous composition is obtained before the microparticles are formed.

Alternatively particles may be prepared, for example by aspirating a solution of active into microspheres in a convection current, from a nozzle with a net electric charge toward a plate or entity with a counter charge, in an anode/cathode type arrangement.

In one embodiment particles employed have a net electric charge, for example a positive charge or negative charge. This may, for example assist the particle's movement being retarded in the target tissue or organ. This net charge may be balanced in the formulation for administration by counter ion spheres (for example without active) of a small dimension, for example less than 5 micron, which are not retained within the target tissue after administration.

In one embodiment the active ingredient is a biological molecule or derived therefrom, for example a protein such as an antibody or a growth factor, a cytokine or combination of entities.

In particular the formulations of the disclosure are, particularly useful for targeting/activating resident stems cells found in the relevant tissue.

In one preferred embodiment the disclosure is used to activate the resident stems, progenitors and/or precursors of a particular tissue or organ to stimulate regeneration of said tissue or organ.

In one embodiment the disclosure relates to localized administration of ligands for the receptors expressed by the stem cells present in the post-natal tissue for initiation of regeneration of the same. The ligand may, for example be a growth hormone as described herein.

In one embodiment the ligands are administered to activate the receptors present on the most undifferentiated stem cells present in each target tissue. These cells express the so-called "multipotency genes", such as Oct 4, Sox2, Nanog, etc. and they have a potent regenerative capacity (hereafter known as Oct4-expressing stem cells).

In one embodiment the ligand is administered to the heart to minimize and/or regenerate tissue damage for example caused by myocardial infraction.

When an artery is obstructed the main effect is a loss of the tissue downstream from the obstruction. The specific consequence of the obstruction of a coronary artery is a myocardial infarction (MI) which results in the irreversible loss of a portion of the cardiac muscle. This loss results in a diminution of the contractile capacity of the myocardium and the pumping capacity of the heart which, when significant enough, limits its capacity to provide the appropriate cardiac output and produces a serious and progressive limitation of the person's capacity (reviewed in Nadal-Ginard et al., Circ. Res. 2003; 92:139).

In the USA and the EU alone over 1.5 million MIs are treated every year and there are over 11 million MI survivors (American Heart Association, 2007; British Heart Association, 2007). Of these, over 30% die during the first year post-infarct. The survival post-MI depends in large measure on the size of the infarct (% of muscle mass lost) due to the ischemic event. When the loss affects ~40-45% of the left ventricular mass it produces an irreversible cardiogenic shock which is uniformly lethal (Page et al., 1971. N. Engl. J. Med. 285; 133). This segmental myocardial loss produces a reorganization of the reminder myocardium with increased cell death by apoptosis, hypertrophy of the surviving myocytes, increased fibrosis of the tissue and dilation of the ventricular chamber (Pfeffer, M. A. & Braunwald, E., 1990. Circulation 81:1161). This reorganization, known as "remodeling", because of its negative effects on contractility, frequently evolves into cardiac failure (CF). After the first episode of CF post-MI the average survival is <5 years with a yearly mortality of ~18% (American Heart Association, 2000).

Most or all the therapies to treat the loss of parenchymal tissue, due to ischemia or to other causes are directed to preserve or improve the function of the surviving tissue. In the case of an MI, all the therapies presently in use to treat the consequences of loss of cardiac contractile muscle are directed to preserve or enhance the contractile function of the surviving tissue and to reduce the continued loss of these muscle cells by apoptosis or by necrosis (see Anversa & Nadal-Ginard, 2002. Nature 415:240; Nadal-Ginard et al. 2003. Circ. Res. 92:139). At present there is not a single approved therapy designed to regenerate or to replace the myocytes lost in the MI and, in this manner, restore the contractile function of the heart. Moreover, all the experimental approaches described until now are directed to improve the blood flow to the ischemic/necrotic area by stimulating the increase in the capillary network, most often by directly or indirectly delivering to the affected area growth factors such as vascular endothelial growth factor (VEGF) either in protein form or in the form of cDNA. Not a single therapy is directed to the resident stem cells in the tissue to stimulate them to multiply and differentiate in order to regenerate together the parenchyma and microcirculation lost by the vascular accident.

The goal of the therapeutic approaches to the acute MI is to restore the blood flow the damaged muscle as soon as possible to prevent further muscle loss. These reperfusion therapies include the use of thrombolytic agents, balloon angioplasty or bypass surgery. In the USA in 1998 >500,000 angioplasties and a similar number of surgical bypasses were performed. These therapies often are successful in restoring blood flow to the ischemic muscle, but none are able to replace a single muscle cell already lost at the time of the intervention. If this loss has been substantial, the long term consequence is an inability to generate the required cardiac output which will inexorably evolve to terminal heart failure.

Until now the only option to effectively treat terminal heart failure has been cardiac transplant with all the medical (immunosuppressive therapy), logistic and economic problems that it entails. Even if these problems could be circumvented, the shortage of donors makes this therapy available to >1% of the patients in cardiac failure.

The formulations of the present disclosure allow the administration of the therapeutically active molecules to be administered in a form where the tissue or organ such as the heart can be targeted specifically to regenerate tissue, for example damaged by obstruction of an artery, by stimulating stem cells already present in the tissue to regenerate.

Stem Cell Therapy for Tissue Regeneration.

Recently some experimental approaches have been developed as alternatives to organ transplantation which are targeted to replace some of the cells lost by the organ or tissue of interest. These procedures have been modeled in the success of the bone marrow transplants carried out for over half a century. The capacity of a small population of cells in the bone marrow to generate all blood cell types, when transplanted in an immunologically competent individual, proved convincingly that adult tissues contained "stem cells" capable to generate and regenerated a tissue or a whole organ. This conceptual breakthrough has led to the developments of experimental approaches to repair damaged tissues using different types of stem cells isolated from the individual to be treated (autologous cell therapy) or isolated from an individual different from the one to receive them (heterologous cell therapy). These cells are either isolated on mass or first expanded in culture before being transplanted to produce the desired repair of the affected tissue. These cell therapy approaches take advantage of the natural regenerative properties of the stem cells for tissue regeneration.

The term "stem cell" is used here to identify a cell that has the properties of self-renewal (generate more cells like itself), is clonogenic (can be expanded starting from a single cell) and it is pluripotent; that is it can produce a progeny which will differentiate into different cell types, often present in the tissue where they reside. That is, the cells originated from a stem cell will acquire particular cellular specializations characteristic of the tissue or organ from which the stem cell originated or into which it is transplanted (Stem Cells: A Primer. 2000. National Institutes of Health USA).

The term "pluripotent" refers to cells which are capable of differentiating into a number of different cell types. In the context of this application the term "tretrapotent" refers to a cell that although it might not be totipotent (capable of generating a whole individual), it is capable to generate four different cell types; e.g. cardiomyocytes, vascular endothelial and smooth muscle cells and connective tissue fibroblasts.

The term "progenitor cell" refers to a descendant of a stem cell which has already committed to a particular differentiation pathway and, therefore, has a more restricted differentiation potential than the stem cell. The progenitor cell has a great capacity of amplification and, although it does not yet express markers of differentiation, it has the capacity to create a progeny that is more differentiated than itself. For example, the term may refer to an undifferentiated cell or to a cell that has differentiated to an extent short of its final differentiation. This cell is capable of proliferation and giving rise to more progenitor cells, therefore having the ability to generate a large number of mother cells that can in turn give rise to differentiated or differentiable daughter cells. In particular, the term progenitor cell refers to a generalized mother cell whose descendants (progeny) specialize, often in different directions, e.g., by acquiring completely individual characters, as occurs in progressive diversification of embryonic cells and tissues. A progenitor cell is more differentiated than a true stem cell because it has already restricted somewhat the multipotency of the stem cell from which it originated.

As used herein unless the context indicates to the contrary stem cell refers to stem cells, progenitor cells and/or precursor cells.

Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors as has been recently demonstrated with the iESCs (induced embryonic stem cells) (Takahashi et al., 2007. Cell 131:1-12).

A "precursor cell" is a descendant of the progenitor cell which has gone further down the differentiation pathway and has become committed to differentiate into a single cell type even though it might not yet express any of the identifiable markers for this cell type. The precursor cell is usually the one undergoing the last round of amplification before the appearance of the identifiable differentiated phenotype.

Stem cells are present in the inner cell mass of the blastocyst, the genital ridges of the early embryo, the placenta and in the majority of tissues of the adult animals, including the human. In contrast to the stem cell derived from the inner cell mass of the blastocyst, in general, the stem cells isolated from adult tissues are a mixture of true stem cells, progenitors and precursors together with cells at the earliest stage of their final differentiation. Adult stem cells have now been identified in practically all tissues originated from each of the three embryonic cell layers (endoderm, mesoderm and ectoderm), ranging from the bone marrow, central and peripheral nervous system, all connective tissues, skin, gut, liver, heart, inner ear, etc.

It appears that these adult stems cells have regenerative capacity. Surprisingly, despite the high prevalence, severity and high economic costs of the ischemic cardiopathy in all developed countries, until recently there has been no search for procedures targeted to the regeneration of the adult myocardium. One of the reasons for this anomaly has been that until very recently the heart was considered a terminally differentiated organ without any intrinsic regenerative capacity of its contractile cells (MacLellan, W. R. & Schneider, M. D. 2000. Annu Rev. Physiol. 62:289; Reinlib. L. and Field, L. 2000. Circulation 101:182; Pasumarthi, K. R. S, and Field, L. J. 2002. Circ. Res. 90:1044; MacLellan, W. R. 2001. J. Mol. Cell. Cardiol. 34:87; Perin, E. C. et al 2003. Ciculation 107: 935; see Anversa, P. and Nadal-Ginard, B. 2002. Nature 415: 240; Nadal-Ginard, B. et al 2003 Circ. Res. 92:139). This concept was based on the experimentally well documented fact that in the adult heart the vast majority of cardiomyocytes are terminally differentiated and their capacity to re-enter the cell cycle has been irreversibly blocked. Thus, there is no doubt that these myocytes are not able to reproduce to generate new myocytes.

One consequence of the prevailing concept of the myocardium as a tissue without regenerative potential has been that all the so-called experimental "regenerative therapies" implemented until now have been based on the introduction within the damaged heart of different cell types that either are fetal myocytes or are believed to have some potential to differentiate into this cell type or into capillaries and microarterioles in order to substitute for the cells lost during the infarct. In this manner animal experiments have been performed transplanting fetal and adult skeletal muscle precursor cells, fetal cardiac myocytes, and embryonic stem cells either in their undifferentiated state or after their commitment to the cardiomyocyte pathway (Kocher et al., 2001. Nature Med. 7: 430).

With the exception of the skeletal muscle precursor (which are incapable of converting to cardiocytes and are unable to become electrically coupled to the myocardial cells) (Menasche et al., 2001. Lancet 357: 279; C Guo et al. 2007. J Thoracic and Cardiovasc Surgery 134:1332) which can be autologous, all other cell types listed are by necessity of heterologous origin and, therefore, have either to be accompanied by immunosuppressive therapy or the transplant is rapidly eliminated by the immune system. The fact is that none of these approaches have proved to be very effective in preclinical assays and all have many pitfalls.

One of the most intriguing characteristics of some of the adult stem cells is their "plasticity". This property refers to the fact that when certain stem cells are placed within a tissue different from the one they originated from, they can adapt to this new environment and differentiate into the cell types characteristic of the host tissue instead of the donor tissue. Although the extent and nature of this plasticity for many cell types still remains controversial (Wagers & Weissman, 2004. Cell 116:636-648; Balsam et al., 2004 Nature 428, 668-673; Murray et al., 2004. Nature 428, 664-668; Chien, 2004. Nature 428, 607-608), it has spawned countless preclinical protocols and clinical trials.

Among the adult stem cells described until now, those from the bone marrow have been the most studied and those that have shown a greater degree of "plasticity" (Kocher et al., 2001. Nature Med. 7: 430). Also widely used have been the so-called "mesenchymal stem cells" derived from adipose tissue (Rangappa, S. et al 2003. Ann. Thorac Surg 75:775).

The capacity of bone marrow and adipose-tissue derived stem cells to re-populate damaged areas of different tissues and organs, the relative ease of their isolation, together with the earlier work of Asahara et al (1999; Circ. Res. 85: 221-228), has proven advantageous for the objectives of cell therapy to regenerate to cardiac muscle in experimental animals (Orlic et al., 2001. Nature 410:701; Orlic et al., 2001. Proc. Natl. Acad. Sci. USA 98:10344; Nadal-Ginard et al., 2003. Circ. Res. 92:139) and in the human (Tse et al., 2003. Lancet 361:47; Perin et al., 2003. Circulation 107:2294). Although it has been questioned by some, (Balsam, L. B. et al. 2004. Nature 428: 668; Murry, C. E. et al. 2004. Nature 428: 664), it is clear that bone marrow derived stem cells under certain conditions are capable to generated cardiomyocytes, capillaries and microarterioles, particularly when transplanted in the border area of an experimental myocardial infarction. (Quaini, F., et al., 2002. New Engl. J. Med. 346:5; Bayes-Geis, A. et al., 2003. Cardiovasc. Res. 56:404; Bayes-Genis, A. et al., 2004. Eur. J. Heart Fail. 6:399; Thiele, H. et al., 2004. Transplantation 77:1902). No similar information is available from the numerous clinical trials of cell therapy with either bone marrow- or adipose tissue-derived stem cells because no reliable histopathological data is available for evaluation.

A major drawback of the techniques used for myocardial cell therapy is the complexity and inefficiency of the cell transplantation procedure itself. When the cells are transplanted through the coronary arterial tree, only 3-5% remains in the myocardium while the rest is spread throughout the body. If the cells are injected directly into the myocardium, it requires either a thoracotomy or the use of complex and time consuming instrumentation (Noga-type systems) in order to identify the target area. This technique requires specialized operators and it is only available in specialized medical centers. In addition, the intramyocardial injections, either by transendocardial (Noga) or transepicardial (surgical) route still delivers <50% of the cells to the tissue.

Without exception, all cell therapy approaches used up to the present time to produce myocardial regeneration post-myocardial infarction either in experimental animals or in the human have been developed completely ignoring the fact that the myocardium has an intrinsic regenerative capacity represented by its resident stem cells (Nadal-Ginard, B., at al., 2003. J. Clin. Invest. 111:1457; Beltrami et al., 2003. Cell 114:763-776; Torella, D., et al., 2004. Circ. Res. 94:514; Mendez-Ferrer, S. et al., 2006. Nature Clin. Prac. Cardiovasc. Med. 3 Suppl 1:S83; Torella et al., 2007. Cell. Mol. Life. Sci. 64:661).

As indicated above, until recently the accepted paradigm considered the adult mammalian heart as a post-mitotic organ without regenerative capacity. Although over the past few years this concept has started to evolve, all the experimental and clinical approaches to myocardial regeneration have continued to be based on the old dogma. For this reason all cardiac regeneration protocols have been based on cell transplantation in order to provide the myocardium with cells with regenerative potential.

It now seems that when formulations of the present disclosure are administered under appropriate conditions that the intrinsic regenerative capacity of the "stem cells" resident in the tissue or organ (such as the heart) can be stimulated or activated to regenerate the tissue or organ.

Thus in one aspect the disclosure provides a method for the regeneration of solid tissues in living mammals, including humans, which include the local delivery of ligands for the receptors expressed by the stem cells present in the post-natal tissue to be regenerated. These are cells that when stimulated physiologically or pharmacologically multiply in situ and differentiate into the parenchymal cells characteristics of the tissue or organ that harbors them.

New cardiomyocyte formation has been detected in both the normal heart and in pathological conditions such as MI and cardiac failure (Beltrami, A. P. et al., 2001. New Engl. J. Med. 344:1750; Urbanek, K. et al., 2003. Proc. Netl. Acad. Sci. USA. 100:10440; Nadal-Ginard, B. et al., 2003. J. Clin. Invest. 111:1457; Nadal-Ginard, B. et al., 2003. Circ. Res. 92:139). Interestingly, these new myocytes are significantly more abundant at the border zone of MIs where they are an order of magnitude more abundant than in the myocardium of age matched healthy individuals. These observations suggested that the adult human myocardium has the capacity to respond to acute and chronic increases in cell death with an abortive regenerative process that attempts to replace the dead myocytes (Anversa, P. & Nadal-Ginard, B. 2002. Nature 415: 240; Anvrsa, P. and Nadal-Ginard, B. 2002. New Engl. J. Med. 346:1410; Nadal-Ginard, B. et al., 2003. Circ. Res. 92:139).

Adult cardiac stem cells (CSCs) were first described in 2003 (Beltrami et al. 2003. Cell 114:763-776) and confirmed by several authors in the same and other species (see Torella, D., et al., 2004. Circ. Res. 94:514; Mendez-Ferrer, S. et al., 2006. Nature Clin. Prac. Cardiovasc. Med. 3 Suppl 1:S83; Torella et al., 2007. Cell. Mol. Life. Sci. 64:661). These CSCs are self-renewing, clonogenic and multipotent because they give rise to cardiomyocytes, endothelial and smooth muscle vascular cells as well as to connective tissue fibroblasts. They were identified by expression of membrane markers associated with stem cells such as c-kit, the receptor for SCF, Sca I, MDR-1 and Isl-I. It is now clear that the new myocytes formed in the adult heart are derived from the CSCs resident in the myocardium. These CSCs, when injected at the border of an infarct, have the capacity to regenerate the contractile cells and the microvasculature lost as a consequence of a massive MI (Beltrami, et al., 2003. Cell: 114:763-776; Laugwitz, et al. 2005; Mendez-Ferrer et al., Torella et al., 2006; Torella et al., 2007).

In the heart of a healthy individual, almost all CSCs are in a resting state ($G_0$) or cycling very slowly during the lifespan of the organism. At any given time, only a very small fraction of these cells is active, undergoing replication and differentiation just enough to replace the cells that die by wear and tear. In contrast, a large fraction of the CSCs—sometimes the majority—is activated in response to a physiological or pathological stress. In general, there is a direct correlation between the magnitude of the stress and the number of CSCs that became activated in response. This number of activated CSCs is in turn also directly correlated to the number of new myocardial cells generated. This response, which occurs from mouse to human (Nadal-Ginard, B. et al., 2003. Circ. Res. 92:139), reveals the existence of a biochemical pathway triggered by the stress that results in the activation of the CSCs.

The communication between the resident stem cells and their environment, at least in the myocardium, is regulated by a feed-back loop between the cardiomyocytes, that sense the changes in wall stress produced by increased physiological or pathological demands in cardiac output, and the stem cells responsible to produce an increase in muscle mass through the generation of new contractile cells and microcirculation to nurture them. The myocytes have a stereotypical response to stress independently of whether it is physiological or pathological (Ellison et al., 2007. J. Biol. Chem. 282: 11397-11409). This response consists in rapidly activating expression and secretion of a large battery of growth factors and cytokines such as HGF (hepatocyte growth factor), IGF-1 (insulin-like growth factor 1), PDGF-$\beta$ (platelet-derived growth factor $\beta$), a family of FGFs (fibroblast growth factor), SDF-1 (stromal cell-derived factor 1), VEGF (vascular endothelial growth factor), erythropoietin (EPO), epidermal growth factor (EGF), activin A and TGF $\beta$ (transforming growth factor $\beta$), WINT3A and neurogeulin among others. This secretory response, in addition to stimulate the hypertrophy of the myocytes themselves through an auto/paracrine loop, also triggers the activation of CSCs in their vicinity because these cells express receptors for these myocyte-secreted factors and respond to them. This response activates genetic pathways downstream of the receptor that are responsible for cell survival, multiplication and differentiation. In addition, the activation of these receptors also activate a feedback loop in the CSCs themselves which stimulates the production of the respective ligand by the CSCs, thus putting in place a self-sustained response which, in response to a single stimulus, can remain active for several weeks or until the increased mass produced has restored the myocardial wall stress to normal levels. Therefore, the CSCs respond to a paracrine stimulus with an auto/paracrine response which allows the maintenance of a sustained response to a short lived stimulation. Thus, normal cardiac cellular homeostasis is maintained through a continuous feed-back between myocytes and CSCs to produce and maintain the appropriate contractile muscle mass required to generated the needed blood cardiac output. The myocytes, which are unable to divide, depend on the CSCs to maintain or increase their cell number and the capillary density to guaranty their oxygen and nutrient supply. The CSCs, on the other hand, depend and respond to the biochemical cues produced by their surrounding myocytes to regulate their resting vs activated state.

In addition to the tissue-specific stem cells described above, we have recently found that the myocardium of mammals, including the human, as well as most other tissues, contain a small population of very undifferentiated cells that have many similarities to the embryonic stem cells (ESCs) which have been known for a long time to be multipotent; that is, a single cell is capable, when placed in the proper environment, to generate a whole organism identical to the one from which it originated. The main characteristic of these cells is their expression of a battery of so-called "multipotency genes" such as Oct4, Sox2, Nanog, etc (see U.S. provisional application Ser. No. 61/127,067) that confer multipotency to these cells, so that, independently of their tissue of origin they seem capable to give rise to most, if not all cell types of the body. In particular, Oct4-expressing cells isolated from the adult heart are capable to give raise to skeletal muscle, neurons, heart, liver, etc. Their regenerative capacity seems more robust and broader than that of the tissue-specific stem cells.

We believe that the Oct4-expressing cells are the origin of most, if not all, the tissue-specific stem cells of every organ and that their stimulation is the main source of the regenerative capacity of every individual tissue. Therefore, the stimulation of these cells is a primary target for the therapeutic approaches described herein.

Independently of their ability and/or efficiency to generate myocardial cells, when a large number of stem cells are introduced into a tissue, regardless of their tissue of origin, they have an important paracrine effect when transplanted into the myocardium and other tissues, as has been proven experimentally. The complex mixture of growth factors and cytokines produced by the transplanted cells have a potent anti-apoptotic effect over the cardiomyocytes and other cells in the area at risk and also in the activation of the endogenous stem cells that multiply and differentiate into muscle cells and microvasculature. This paracrine effect starts very soon after the cell transplantation and can be documented in vitro.

It seems from the work performed in the examples herein that to stimulate the resident stem cells of a tissue (including the Oct4 expressing cells), in this case the myocardium, the growth factors and cytokines produced by the stressed myocytes and to which the CSCs respond could be as or more effective than cell transplantation to trigger a regenerative response. A combination of insulin-like growth factor 1 and hepatocyte growth factor may be particularly effective.

In one embodiment resident stems cell are activated, for example to stimulate regeneration of the tissue, to increase muscle density and/or cell function of target cells.

If the target cells are cardiac muscle then the increased function would, for example be greater/increase contractile function.

If the target cells are kidney cells, in a renal failure kidney patient, then the increased function may be increased capacity to generate EPO.

If the target cells are pancreatic cells then the increased function may be increased capacity to generate insulin.

It seems that formulations of the disclosure are able to stimulate/activate stems cells resident in "mature tissue" thereby obviating the need to administer "stem-cell" therapy to the patient as the resident stems are stimulated to undergo mitosis and grow.

Stimulating resident stems cells is distinct from angiogenesis. Angiogenesis is the process of stimulating growth of capillaries (which may be in tissue or tumors) (see Husnain, K. H. et al. 2004. J. Mol. Med. 82:539; Folkman, J., and D'Amore, P. A. 1996. Cell 87:1153). In contrast, when formulations of the present disclosure employing appropriate ligands are administered a stem cells resident in the tissue, such as pluripotent cells, progenitor cells and/or a precursor cells are activated to generate new/additional tissue cells such as muscle cells.

All the regenerative approaches described until now have severe limitations either because of the nature of their biological target, the regenerative agent used and/or the route and mode of administration. The vast majority of so-called regenerative therapies have been directed to regenerate the capillary network of the ischemic myocardium using a variety of biological factors, such as vascular endothelial growth factor (VEGF), whose main role is to stimulate the growth of the surviving endothelial cells in the damaged tissue in order to expand the capillary network and improve the blood supply (Isner, J. M. and Losordo, D. W. 1999. Nature Medicine 5:491; Yamaguchi, J., et al., 2003. Circulation 107:1322; Henry, T. D., et al., 2003. Circulation 2003. 107:1359). These therapies neither attempt nor accomplish the regeneration of the parenchymal cells that perform the characteristic function of the tissue or organ; e.g. contractile cardiomyocytes in the heart, hepatocytes in the liver, insulin-producing β cells in the pancreas, etc. At best, these therapies have had modest effects and none of them has become part of standard medical practice. On the other hand, all the regenerative therapies designed to replace the functional cells of the tissue or organ have until now been based in the transplantation of cells believed to be able to take on the characteristics of the missing cells in the target tissue. These approaches are still in clinical trials. A main drawback for all the regenerative approaches used has been to deliver the regenerative agent to the damaged tissue and limit their spread throughout the rest of the body. This is a serious problem even when the regenerative agents are administered through the coronary arterial tree of the tissue to the treated. In the cases of myocardial cell therapy by coronary administration, only a very small fraction of the cells administered is retained in the heart, while the majority (>95%) rapidly enters the systemic circulation and it is distributed throughout the body. This also occurs when the regenerative agents are directly injected into the myocardium either trans-epicardially or trans-endocardially, as has been repeatedly demonstrated with the administration of a cell suspension. In addition, the trans-epicardial administration requires exposing the heart through a thoracotomy, while the trans-endocardial administration requires a sophisticated, time consuming and expensive procedure to map the endocardium to identify the regions suitable for injection (a Noga-type instrument), a procedure available in a very limited number of centers and the participation of an expert manipulator. In both cases, at best 50% of the administered compound is retained in the damaged are while the remainder is spread either throughout the thoracic cavity or through the systemic circulation. The formulations of the disclosure may be used in combination with the delivery of stems cells to a target tissue or organ and increase the number that are retained locally in comparison to other delivery mechanisms.

However, this disclosure describes a novel method to regenerate the parenchymal cells (that is, the functional, "noble" cells) of a tissue or organ that is based neither on cell transplantation nor on the growth stimulation of the surviving endothelial cells in order to improve the blood supply to the tissue or organ of interest. Instead, the methods described here are based in the stimulation in situ, that is, within the tissue, of the resident stem cells of such tissue by means of local delivery of specific growth factors and/or cytokines which are able to stimulate their activation, replication and differentiation to generate the parenchymal cells lost as well as the microvasculature needed for their growth, survival and function. This is possible because most, if not all adult tissues mammalian tissues, including human tissue, contain resident stem cells which are capable, when properly stimulated, of regenerating the cell types which are specific to the tissue or organ, as well as the vascular and mesenchymal supporting cells which accompany them.

Because some of the regenerative agents that stimulate the stem cells are very active and might stimulate the growth and translocation of a variety of cells they interact with, among them latent neoplastic cells, the potential clinical application of many of these factors will require the administration of the smallest therapeutic doses in a very localized manner in order to, as much as possible, limit exposure to the cells that are to be regenerated. Thus, the more localized the administration the lower the doses required and lower the risk of undesired side effect due to stimulation of by-stander cells in the same or other organs. More specifically, the disclosure describes a new approach for the use of therapeutic doses of different growth factors administered and delivered locally, instead of systemically or tissue-wide, to produce the regeneration of specific areas of a solid tissue. Because the delivery of the active compound is localized to the damaged tissue, the therapeutic dose required is a minute fraction of what would be needed with other available delivery methods. The formulation of the disclosure is capable, among others applications, to regenerate the heart muscle and its microvasculature after a myocardial infarction and/or in chronic cardiac failure.

In one embodiment the formulation is administered at the border of the damaged tissue, for example at the border or an ischemic zone.

Suitable ligands for stems cells include growth factors such as those listed in Table 1

TABLE 1

| Examples of suitable stem cell ligands of the invention |
| --- |
| HGF (hepatocyte growth factor), |
| IGF (insulin-like growth factor) such as IGF-1, |
| PDGF (Platelet-derived growth factor) such as PDGF-β, |
| FGF (fibroblast growth factor) such as aFGF (FGF-1) or bFGF (FGF-2) and FGF-4, |
| SDF-1 (stromal cell-derived factor 1), |
| EGF (epidermal growth factor) |
| VEGF (vascular endothelial growth factor), |
| erythropoietin (EPO), |
| TGF β (transforming growth factor β), |
| G-CSF (Granulocyte-colony stimulating factor), |
| GM-CSF (Granulocyte-macrophage colony stimulating factor), |
| Bone morphogenetic proteins (BMPs, BMP-2, BMP-4) |
| Activin A, |
| IL-6, |
| Neurotrophins for example NGF (Nerve growth factor), neuroregulin, BDNF (brain-derived neurotrophic factor), NT-3 (neurotrophin-3), NT-4 (neurotrophin-4) and (neurotrophin-1), which is structurally unrelated to NGF, BDNF, NT-3 and NT-4 |
| TPO (Thrombopoietin) |
| GDF-8 (Myostatin), or |
| GDF9 (Growth differentiation factor-9). |
| Periostin |

In one embodiment the growth factor(s) employed is human.

In one embodiment the growth factor employed is selected from HGF, IGF (such as IGF-1 and/or IGF-2) and FGF, in particular HGF and IGF-1. These factors appear to be particularly effective in stimulating resident stem cells.

Combinations of growth factors may also be employed and, for example may be selected from the above-identified list, such as HGF and IGF-1 and optionally VEGF.

In one embodiment the formulation for regenerating/activating stems cells does not consist of VEGF as the only active but for example may comprise a combination of actives include VEGF.

Nevertheless the formulation is suitable for localized delivery of VEGF as angiogenesis factor.

In one embodiment the growth factor formulation is employed in combination with an angiogenesis factor, for example administered concomitantly or sequentially by the same route or a different route.

In one embodiment the formulation comprises a cytokine, for example selected from IL-1, IL-2, IL-6, IL-10, IL-17, IL-18 and/or interferon.

In one embodiment the formulation comprises combinations of actives, for example a growth factor and a cytokine.

In combination formulations then the dose of each active may, for example be the same dose employed when the active is administered alone.

The components employed in the formulations and/or methods of the disclosure, especially biological type actives may be derived from natural origin.

In one embodiment a biological type active employed is prepared by recombinant DNA technology.

In one embodiment the active or actives administered may be peptide fragments of a biological molecule, with the desired therapeutic effect.

In one or more embodiments the molecules employed are mutants of a biological molecule (for example a ligand of a receptor) with the desired therapeutic effect having the same, higher or lower affinity for the corresponding biological molecule.

In one embodiment the substance(s)/active employed is an aptomer (a small RNA molecule that binds to a receptor instead of the natural ligand).

In one embodiment the substance/active employed is an antibody that recognizes and binds to a target receptor, and in particular has a suitable specificity and/or avidity for the same. Desirably the antibody has the required activity to upregulate the receptor or down regulates the receptor thereby either producing activation or blocking of the same, as appropriate.

In one embodiment the active is a diaquine, which is an artificial antibody molecule that recognizes and binds to two of the receptors of interest resulting in either the activation or blocking of one and/or the other.

In one embodiment the substance/active employed is a small molecule with a molecular weight <5,000 Daltons.

In one embodiment one or more actives employed may be of synthetic origin.

For the formulation disclosed herein to target the desired organ or tissue then the formulation should be administered upstream of the organ or tissue. That is to say should be introduced into the circulation such that the flow of blood carries the formulation into the desired tissue/organ.

The formulation can be introduced upstream of an organ such as the heart employing a suitable device such as a catheter. Other major organs can be reached in this way. Similarly whilst is it rare it is also possible to use catheters to gain access to the liver.

In other instances the formulation may be introduced by strategic intra-arterial injection or by retrograde venous injection and/or cannular before the target tissue.

The formulation may also be administered by infusion or a pump driven delivery device such as a syringe pump, for example of the type employed in the administration of heparin or morphine or contrast agents during catheterization. A suitable flow rate may for example be 0.5 mL/min.

The formulation might also be administered through the so-called perfusion catheters that allow slowing down the rate of blood flow downstream from the site of the injection with an intra-arterial balloon, while maintaining perfusion of the tissue through a second lumen of the catheter.

In a particularly suitable embodiment the formulation is administered into an artery upstream of the target tissue or organ.

In one embodiment a catheter is used to deliver the formulation of the disclosure into the artery supplying the target tissue or organ. In particular, the formulation may be delivered exclusively (primarily or substantially) to the segmental artery that supplies the area of the tissue or organ.

In one embodiment the catheter employed is a balloon catheter.

In one embodiment the catheter carries a filter mesh at its distal end with a pore size sufficiently small to prevent or hinder the release of microparticle aggregates >50, 25 or 20 μm, as required.

In one embodiment the target cells are the cardiac stem cells resident in the post-natal heart.

In one embodiment the regeneration obtained includes together or separately the regeneration of cardiomyocytes and vascular structures composed of capillaries (endothelial cells) and/or arterioles (endothelium and vascular smooth muscle cells).

In one embodiment the regeneration is induced at any time after a myocardial infarction (MI) be it acute or chronic, for example 0.5, 1, 1.5, 2, 2.5, 3, 3.5, 4, 4.5, 5, 5.5, 6, 6.5, 7, 7.5, 8, 8.5, 9, 9.5, 10, 10.5, 11 up to 24 hours after an acute infarction.

In one embodiment the regeneration is induced in an individual with ischemic heart disease, with or without a myocardial infarction.

In one embodiment the regeneration is induced in the hearts of individuals that have developed cardiac failure (CF) either acute or chronic.

In one embodiment the regeneration is induced in individuals with ischemic, infectious, degenerative or idiopathic cardiomyopathy.

In one embodiment the target cells are the stem cells resident in the endocrine pancreas (stem cells of the islands of Langerhans).

In one embodiment the regeneration is induced in an individual with diabetes.

In one embodiment the target cells are the neural stem cells of the central nervous system (CNS).

In one embodiment the target stem cells are the neural stem cells of the spinal cord.

In one embodiment the regeneration is induced in an individual with a spinal cord lesion.

In one embodiment the target cells are the stem cells of the substantia nigra of the brain, for example in an individual with Parkinson's disease.

In one embodiment the regeneration is induced in an individual with a cerebral vascular accident (stroke).

Whilst not wishing to be bound by theory it is believed that the ligands employed in formulations of the disclosure are able to cross the blood brain barrier to treat strokes and the like. In addition, in cerebral vascular accident it is believed that the blood brain barrier becomes impaired and chemical entities can more readily pass through the barrier.

In one embodiment the target cells are the liver stem cells and for example the regeneration is induced in an individual with liver damage such as cirrhosis.

In one embodiment the target stem cells are the stem cells of the lung(s) and for example the regeneration is induced in a patient with lung damage, for example emphysema.

In one embodiment the target cells are the stem cells of the skeletal muscle and for example the regeneration is induced in an individual with a particular skeletal muscle deficit, such as osteoporosis or pagets disease.

In one embodiment the target cells are the stem cells of the epithelium.

In one embodiment the target stem cells are the stem cell of the kidneys.

Target cells as employed herein refers to the cells that are to be stimulated and which have the potential to provide the desired regeneration.

The formulation of the disclosure provides optimized parameters and materials to ensure accurate and/or reproducible dosing of the relevant active to the target tissue or organ.

In an alternative embodiment the formulations of the disclosure may be employed to treat solid tumors, by allowing local delivery of the antineoplastic to the tumor tissue, for example by intra-tumor injection.

Actives suitable for the treatment of tumors include etoposide, cyclophosphamide, genistein, cisplatin, andriamycin, vindesine, mitoguazone, fluorouracil and paclitaxil.

In one embodiment the formulation is not for the treatment of cancer.

In one embodiment the invention is not administration directly into a tumor or tissue.

The methods according to the disclosure may employ combinations of actives administered separately, for example concomitantly or sequentially, or formulated as one (one-pot) formulation.

Formulations of the disclosure may be administered as liquid solutions/suspension, for example in an isotonic carrier, for example as a buffered solution such as phosphate buffer, saline or glucose solution.

Formulations of the disclosure may optionally comprise one or more further excipients. The excipients should be suitable for administration to humans and/or animals.

In one embodiment the formulation comprises albumin in solution, which may for example stabilize the small quantities of active in the formulations, for example from 1% to 20% w/vol of albumin, such as human serum album, may be sufficient to achieve the required stabilization.

The disclosure also extends to use of as a formulation as defined herein for treatment, particularly for the treatment of myocardial infarction; ischemic heart disease; cardiac failure; ischemic, infectious, degenerative or idiopathic cardiomyopathy, sclerosis, cirrhosis, emphysema, diabetes and the like.

In one embodiment the disclosure relates to a formulation as described herein for use in treatment, particularly for treatment of an illness described above.

The disclosure also extends to methods of treatment comprising administering a therapeutically effective amount of a formulation described herein to a patient in need thereof, particularly for the treatment of a disease described above.

The disclosure also extends to use of a ligand, for example as described herein, for stimulating a resident stem cell in vivo to activate the cell.

The disclosure also includes uses of a suitable growth factor for the manufacture of a medicament for stimulate resident stem cells in vivo.

The disclosure will now be illustrated by reference to the Examples.

EXAMPLES

Introduction

Anterior myocardial infarctions were produced in female pigs by temporary balloon occlusion of the anterior descending coronary artery distal to the first septal branch. This procedure resulted in anterior-apical infarctions of reproducible moderate size. The myocardial regeneration potential of combined insulin-like growth factor 1 and hepatocyte growth factor was tested by locally administering the factors at different doses in the infarcted pig myocardium. Control animals were treated with placebo.

The feasibility to produce therapeutic effects with local administration of minute amounts of therapeutic agents was tested first by direct administration of a solution containing a mixture of recombinant human IGF-1 and HGF in the acute post-MI produced in an experimental model with closed chest by balloon dilation in the anterior descending left coronary artery just below the emergence of the first septal artery in 23 pigs that were compared to 6 placebo controls identically treated.

Materials and Methods

The hearts were analyzed at different time points after myocardial infarction, ranging from a few days to 1 month. The results showed a dramatic increase in the number of activated stem and progenitor cells in the ischemic area and its borders of pigs treated with human IGF-1 and HGF. Notable regeneration of the muscle was seen in the ischemic area, which also contained newly formed arterioles and vessels. The regenerative response seemed to be proportional to the doses of growth factors administered. From these preliminary data, therapeutic in situ activation of CSCs can produce extensive new myocardial tissue formation and significantly improve left ventricular function in animal hearts that are similar in size and anatomy to human hearts.

Isolation of c-kit$^{pos}$ Porcine Cardiac Cells

Multiple cardiac samples (~2 g each) were obtained from different cardiac regions (right and left atria, right and left ventricle and apex) of female Yorkshire white pigs (23±4 kg; n=3). Some samples were fixed and embedded in paraffin for histochemical analysis. The other pieces were enzymatically digested and cardiomyocyte-depleted cardiac cell suspensions were prepared as previously described with modifications (Beltrami, A. P. et al., 2003. Cell 114:763). Briefly, minced cardiac tissue was digested with 0.1% collagenase (Worthington Biochemicals), 0.1% Trypsin (Sigma), 0.1% DNAse I in Hanks' balanced salt solution (HBSS) buffer at 37° C. and the small cardiac cell fraction collected through centrifugation. Cardiac small cells were incubated with anti-human CD117(c-kit) Ab (Miltentyi Biotechnology) and sorted by fluorescence-activated cell sorting (FACS; MoFlo (Dako Cytomation) cell sorter) or magnetic activated microimmunobeads (MACS). Propidium iodide (PI; 2 µg/mL) was added before FACS to exclude dead cells.

c-kit$^{pos}$ porcine cardiac cells were analysed for hematopoietic, mesenchymal and endothelial cell markers using a FacsCalibur flow cytometer (Becton Dickinson, BD). Antibodies used were anti-porcine CD45 (Serotec, Clon: MCA1447), anti-human CD34 (BD, don 8G12), anti-human CD90, (BD, Clon:5E10, pig cross-reactivity) and anti-human CD166 (BD, Clon: 3A6, pig cross-reactivity), anti-human CD105 (Caltag Laboratories, Clon: SN6, pig cross-reactivity) and anti-human CD133 (Miltenyi Biotec, cion AC133, pig cross-reactivity). Anti-human antibodies specific to PECAM, E-cadherin, CD11b, CD13, CD14, CD29, CD31, CD33, CD36, CD38, CD44, CD49, CD62, CD71, CD73, CD106, were purchased from BD Biosciences. Respective isotype controls (Pharmingen) were used as negative controls for all FACS procedures. Data were analysed using the CellQuest software.

Porcine c-kit$^{pos}$ Cardiac Cell Culture, Cloning, and Differentiation Potential c-kit$^{pos}$ cells were plated for 7-10 days at $2 \times 10^4$ cells/ml in Dulbecco's MEM/Ham's F12 (DMEM/F12) modified medium containing 10% FBS, bFGF (10 ng/ml), insulin-transferrin-selenite (ITS), and EPO (2.5U). After recovery, some cells were moved to a modified cardiosphere formation media (mCSFM): 1:1 ratio of DMEM/F12, bFGF (10 ng/ml), EGF (20 ng/ml), ITS, 2-β-mercapethanol (0.1 mM) and Neural Basal Media supplemented with B27 and N2 supplements (Gibco), for the generation of cardiospheres. To test for clonogenicity, single c-kit$^{pos}$ cells were seeded individually into wells of 96-well gelatin coated Terasaki plates by flow cytometry or serial dilution. Individual c-kit$^{pos}$ cells were grown in DMEM/F12 modified medium for 1-3 weeks when clones were identified and expanded. The clonogenicity of the ckit$^{pos}$ cells was determined by counting the number of clones generated in each 96-well plate and expressed as a percentage. A total of 10 plates per cardiac region were analyzed. Clonogenic cells and cardiospheres were transferred to a specific cardiogenic differentiation medium (modified from 42) for myocyte, vascular smooth muscle and endothelial cell specification.

The cell migration assay was carried out using a modified Boyden chamber, according manufacturer's instructions (Chemicon). 200 ng/ml HGF or 200 ng/ml IGF-1 were placed in the lower chamber of a 24 well plate for 24 hours. For proliferation assay, $2.5 \times 10^4$ pCSCs were plated in 24×35 mm dishes and were serum starved for 36 hrs in 0% serum DMEM/F12 base medium. 6 dishes acted as baseline control and were supplemented with BrdU (1 ug/ml) before being fixed and stained 1 hour later. Then DMEM/F12 base medium supplemented with 3% FBS and 200 ng/mlHGF (n=6 dishes) or 200 ng/ml IGF-1 (n=6 dishes) was added to the remaining 12 dishes. 6 dishes acted as controls, with no growth factors added to the medium. BrdU was added, 1 µg/ml every 6 hours. Cells were fixed after 24 hours and BrdU incorporation was assessed using the BrdU detection system kit (Roche). The nuclei were counterstained with the DNA binding dye, 4,6-diamidino-2-phenylindole (DAPI, Sigma) at 1 µg/ml. Cells were evaluated using fluorescence microscopy (Nikon E1000M). 10 random fields at ×20 magnification were counted for each dish, and numbers expressed as a percentage of BrdU positive cells relative to the total number of cells counted.

Immunocytochemistry

Cells were cultured on glass chamber slides (BD Falcon) for 2 days, fixed with 4% PFA for 20 min, and then stained. For intracellular staining, cells were permeabilized using 0.1% Triton X-100. Cells were incubated with the primary antibody overnight at 4° C., washed three times and then incubated with a FITC- or Texas Red-conjugated secondary antibody for 1 hr at 37° C. Then cells were washed three times, and nuclei were counterstained with DAPI. Fluorescence was visualized and images acquired with confocal microscopy (Zeiss LSM510). The following antibodies were used for cell staining: Oct3/4, Nanog, Is1-1, c-kit, Flk-1, and NRx2.5 (R&D Systems); Bmi-1, c-met and IGF-1r (Santa Cruz Biotechnology), telomerase (Abeam). Cardiospheres were stained for c-kit after 24 hours of culture in a glass chamber slide. After 4-6 days in culture to allow outgrowth and differentiation of cells from sphere, they were stained with antibodies against smooth muscle actin, α-sarcomeric actin (Sigma) and von Willebrand factor (DAKO). All secondary antibodies were purchased from Jackson Immunoresearch.

Western Blot Analysis

Immunoblots to detect the IGF-1 (IGF-1R) and HGF (c-met) receptors were carried out as previously described (Ellison et al. 2007. J. Biol. Chem. 282:11397) using protein lysates obtained from c-kit$^{pos}$ pCSCs subjected to serum starvation medium for 24 hours followed by supplementation with 200 ng/ml IGF-1 or 200 ng/mlHGF for 10-20 minutes. The following antibodies were used at dilutions suggested by the manufacturers: rabbit polyclonal Abs IGF-1R, phosphor-IGF1R, Akt, phosphor-Akt, c-met (Cell Signalling), phosphor-c-met (Abcam), FAK, and phosphor-FAK (Upstate).

Histology

After atrial excision hearts were divided into 5 coronal slices from apex to base with cuts perpendicular to the long axis. Samples of infarcted, peri-infarcted and distal myocardium were obtained from each level from each pig. Samples were washed with PBS, fixed in 10% formalin and paraffin embedded. 5 µm sections were prepared on a microtome (Sakura) and mounted on microscope slides. Sections were stained with hematoxylin and eosin (H&E), according to standard procedures (Ellison et al. 2007. J. Biol. Chem. 282: 11397). Myocyte diameter was measured across the nucleus in H&E sections (3 slides per animal) of the peri-infarct region from levels C and D, on a light microscope (Nikon E1000M) using Lucia G software. A total of 200 myocytes per section were analyzed for each pig.

To determine myocardial fibrosis, sections of the infracted myocardium were stained with Sirius red as previously described (Lee, C. G. et al., 2001. J. Exp. Med. 194:809). Serial sections were fixed in 10% formalin in PBS for 20 min After washing in distilled water for 5 min, sections were incubated at room temperature for 30 min in 0.1% Fast Blue RR in Magnesium Borate buffer at pH 9 (Sigma). Then sections were washed in distilled water before incubation at room temperature for 10 min in 0.1% Sirius red in saturated picric acid (Sigma). Sections were further washed in distilled water before they were dehydrated, cleared and mounted. In this protocol, connective tissue (mainly collagen) stains red and muscle stains yellow/orange. Semi-quantitative evaluation of the amount of myocardial connective tissue was carried out using Lucia G image analysis at ×40 magnification. Percent collagen (percent area of positive staining) was determined in the entire infarct zone. A total of 3 slides were assessed per animal for each level, and an average obtained.

Immunohisochemistry and Confocal Microscopy

To identify CSCs, transverse pig heart sections were stained with antibodies against the stem cell antigen, c-kit (rabbit polyclonal, Dako). c-kit$^{pos}$ CSCs were identified as lineage-negative (Lin$^{neg}$), by staining negative for markers of haematopoietic, neural, and skeletal muscle lineages (21). For quantification of CSC myocardial distribution in the different cardiac regions of control pigs, the number of c-kit$^{pos}$ (lin$^{neg}$) cells and cardiomyocytes was counted for a total of 5 sections at ×63 magnification. The area of each cross section was then measured, and the number of CSCs and cardiomyocytes per unit area was determined. The data for the atria were pooled, due to few differences found between the number of c-kit$^{pos}$ CSCs in the left and right atria. The number of CSCs was expressed per $10^6$ myocytes.

Cycling cells were identified by BrdU (Roche) and Ki67 (Vector labs) staining. Progenitor cells stained positive for c-kit and the transcription factors, NRx2.5 (R&D Systems), Ets-1 and GATA6 (Santa Cruz Biotechnology). Newly formed myocytes were identified with antibodies against BrdU, Ki67 and α-sarcomeric actin (Sigma), cardiac troponin I (Santa Cruz Biotechnology) or slow (cardiac) myosin heavy chain (Sigma). Newly formed vascular structures were detected by staining for BrdU and α-smooth muscle actin (mouse monoclonal, Sigma) or vWF (rabbit polyconal, Dako). Images were acquired using confocal microscopy (Zeiss 510 LSM). The number of CSCs, myocyte progenitor cells (c-kit$^{pos}$/NRx2.5$^{pos}$, and newly formed myocytes (BrdU$^{pos}$ and ki67$^{pos}$ were quantified for the infarct, peri-infarct and distal regions in each level. A total of 3000 cells (~20 fields) were counted for each region at x63 magnification. 3 slides per animal were assessed. Numbers were expressed as a percentage relative to the total number of cells counted. The size of 50 BrdU$^{pos}$ newly formed myocytes per animal in the infarct and peri-infarct regions was measured using Lucia G software.

The density of capillaries in the infarct region was evaluated by staining with an antibody against vWF (DAKO). The 2° Ab used was a donkey anti-rabbit, conjugated with HRP (Santa Cruz). Endogenous peroxidase in the section was blocked with 3% hydrogen peroxide in PBS for 15 minutes at room temperature. The chromogen 3, 3-diaminobenzidine (DAB) (Sigma) was used to visualize the blood vessels. The slides were counterstained with hematoxylin for identification of nuclei. The number of capillaries (defined as 1 or 2 endothelial cells spanning the vWF-positive vessel circumference) was determined by counting 10 fields/section in the infarct zone in levels C and D at ×40 magnification. A total of 3 slides/animal were assessed. The number of capillaries was expressed per 0.2 mm$^2$.

To detect cellular apoptosis, sections were stained with rabbit anti-human activated caspase-3 primary antibody (R&D Systems) and a donkey anti-rabbit HRP-conjugated 2° Ab. The chromogen DAB (Sigma) were used to visualise the apoptotic cardiomyocytes. Sections were then counterstained with haematoxylin and permanently mounted before being examined by light microscopy. The number of caspase-3 positive myocytes in the peri-infarct zone of levels C and D was determining by counting 20 random fields/section at ×40 magnification. A total of 3 slides/animal were assessed. The amount of caspase-3 positive myocytes was expressed as percentage relative to the total number of myocytes counted.

Statistical Analysis

Data are reported as Mean±SD. Significance between 2 groups was determined by Student's t test and in multiple comparisons by the analysis of variance (ANOVA). Bonferroni post hoc method was used to locate the differences. Significance was set at P<0.05.

Example 1

Preparation of PLGA Microspheres

Two sets of microspheres of PLGA and alginate were prepared; one set containing a mixture of human serum albumin (HSA) and insulin-like growth factor 1 (IGF-1), the other set containing a mixture of HSA and hepatocyte growth factor (HGF). The HSA was used to provide enough bulk for the emulsion given the very small quantities of the growth factors needed.

The conditions used to form the PLGA microspheres are the following:

A nebulizer Flow Focussing of Ingeniatrics (D=150 µm, H=125) was employed in a configuration liquid-liquid in which the focused liquid is the emulsion of PLGA+HSA+growth factor and the focusing liquid is water.

The lipid phase consisted of: 5% PLGA in EtOAc (ethyl acetate)

The aqueous phase consisted of: 5% HSA, 0.1% growth factor, 0.45% NaCL, 0.25% Tween 20 in H2O.

The mixture of the two phases was sonicated for 30 min

The microdroplets are produced in a bath of 2% polyvinyl alcohol (PVA, Fluka Chemica).

The size of the particles is controlled by the flow volume of the focused ($Q_d$) and focusing ($Q_f$) fluids. To obtain particles of 15±1 microns, a $Q_d$=3 5 mL/h and a $Q_f$=3 mL/h were used. The efficiency of encapsulation of HSA+IGF-1 mixture was of 37%.

Figure 8:
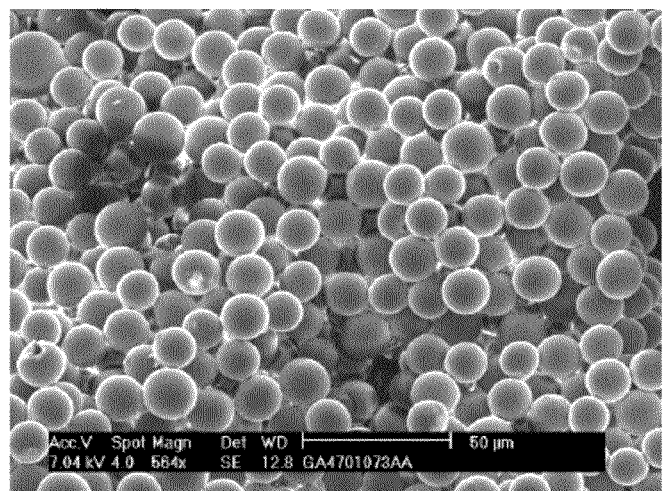
FIG. 8 shows an electron micrograph of PLGA particles with IGF-1 prepared as per Example 1 and shown in FIG. 7.

The size of the particles was ascertained by optical and electron microscopy (see FIG. 8).

The same procedures with minor modification were used to prepare HGF-containing PLGA particles.

Example 2

Optimization the Production of Monodisperse PLGA Microspheres of 15 µm Diameter

To optimize the efficiency of encapsulation in order to reduce the number of microspheres to be administered the conditions used were optimized with modification in the following parameters:

a.—Incorporation of emulsifiers in the lipid phase. The optimal combination was found to be a mixture of Tween 80 and Span 60 which produced emulsion stable for up to 5 hours.

b.—Optimization of the concentration of protein (Human Serum Albumin), HSA of 20% instead of 5%.

c.—Optimization of the concentration of NaCl in the aqueous phase to 0.2% instead of 0.45%.

d.—Optimization of the PLGA concentration to 5.5% instead of 5% in EtOAc.

e.—The concentration of HGF-1 in the initial mix was 0.4%

Therefore the aqueous phase consisted of 20% HSA, 0.4% IGF-1; 0.2 NaCl; 0.1 Tween 20; 0.15 Span 60. The organic phase consisted of 5.5% PLGA in EtOAc (ethyl acetate).

The microparticles were obtained by simple flow focusing the conditions described in Example #1.

The size of the particles, as determined by SEM was of 14.36 µm with a SD of 0.91 and an efficiency of encapsulation of 82.4 with an entrapment of 13.1%. Protein determinations complemented by quantitative ELISAs documented that each 1×10$^6$ microspheres carried 3 µg of IGF-1 and 348 µg of HSA. Biological in vitro assays of the IGF-1 contained in the microspheres tested by their capacity to bind and activate the IGF-1 receptor of live cells show that after one round of liophylization and resuspension the encapsulated IGF-1 maintained 82% of the original biological activity. Therefore, each one million of microspheres had a biological activity equivalent of 2.5 ng of the native IGF-1.

Similar protocols were used to encapsulate HGF, with a final result of 1.7 µg HGF encapsulated per 1×10$^6$ particles with a biological activity of 63% of the original. Thus, each million of HGF microspheres can deliver the equivalent of 1 µg of active HGF.

The encapsulation of SCF (Stem Cell Factor), the ligand for the c-kit receptor, produced particles containing 2.3 µg SCF per 1×10$^6$ microspheres with an activity 76% of the original solution as determined through activation of the c-kit receptor.

Conclusion:

The single flow focusing procedure used is very efficient in the encapsulation of a mixture of HSA and different growth factors. Changing the initial ratio of HSA to growth factor it is possible to reach loading values of up to 350 μg of the desired pharmacological protein per $1\times10^6$ microspheres of PLGA of 15 μm of diameter with a variation coefficient of ≤6%.

Example 3

Production of Monodisperse ALGINATE Microspheres and Encapsulation of IGF-1

The reagents and equipment used for the production of the microspheres were the following:
Alginate: Protanal LF 10/60; FMCBioPolymer (G/M≥1.5); Protanal LF10/60LS; FMCBioPolymer (G/M≤1).
HSA (human serum albumin, 97-99%, A9511) from Sigma-Aldrich
IGF-1 from PreProtect
$CaCl_2$; tribasic sodium citrate
Nebulizers FF simple in the configuration liquid-gas: L2 (D=100 μm, H=100) and L3 (D=100 μm, H=100).
Harvard pump 11 plus.

After more than 120 assays to establish the appropriate conditions, it became evident that a mixture of alginates gave better results than a single alginate. Protanal LF10/60: Protanal LF10/60LS at a ratio 0.7%:0.3% gave the optimal results. The optimal distance for nebulization was found to be 10 cm. The optimal concentration of HAS in the mix was 14% and IGF-1 0.3%. This mixture is nebulized using the FF (D=100 μm, H=100) in configuration liquid-gas (ΔPt=300 mbar, $Q_d$=5 mL/h using gas as the focusing fluid. The nebulizer is placed at 10 cm of a solution of 3% $CaCl_2$ in a shaking bath, collected by centrifugation after 30 min and washed to remove the $CaCl_2$. The size distribution of the particles is determined by flow cytometry and SEM. The efficiency of encapsulation of HSA by protein quantification and standard curves. The encapsulation of hrHGF-1 was determined by ELISA as described in Example #2.

The size of the particles, as determined by SEM was of 15.87 μm with a SD of 1.83 and an efficiency of encapsulation of 71.4 with an entrapment of 11.6%. Protein determinations complemented by quantitative ELISAs documented that each $1\times10^6$ microspheres carried ~2 μg of IGF-1 and 269 μg of HSA. Biological in vitro assays of the IGF-1 contained in the microspheres tested by their capacity to bind and activate the IGF-1 receptor of live cells show that after one round of liophylization and resuspension the encapsulated IGF-1 maintained 67% of the original biological activity. Therefore, each one million of microspheres had a biological activity equivalent of ~1.5 μg of the native IGF-1

This protocol can be adapted to be used with different types of polymers such as Polyether-polyester segmented block copolymers of polybutylene terephthalate (PBT) and polyethylene oxide (PEO) PolyActive® using the FF nebulizer as well as other spraying methods.

Conclusion:

Alginate is an adequate polymer for the production of monodisperse microspheres with an approximate diameter of 15 μm and to encapsulate large amounts of proteins. The protocols used can be modified to increase the ratio of IGF-1 to HSA up to 60:40 which increases the load of active compound by more than two orders of magnitude. From the results obtained, the range of sizes around the peak of 15 μm is narrower when using PLGA than with the combination of alginates tested here. Given the large number of different alginate preparations it is likely that the homogeneity of the microparticles found here could be significantly improved.

Example 4

To produce microspheres where the active compound is located on the surface of the particle it is possible to produce the microspheres shown above using a polyelectrolyte instead of PLGA of charge of opposite sign to the active to be bound. Examples of such polyelectrolytes are gum Arabic, pectins, proteins, nucleic acids, polysaccharides, hyaluronic acid, heparin, carboxymethylcellulose, chitosan, alginic acid and a multitude of synthetic polymers. When the polyelectrolyte has a charge of opposite sign to the active compound, it is possible to attach it to the microparticle by absorption from a solution of the active.

Example 5

Microspheres of 15 μg in Diameter are Optimal for Capillary Entrapment after Intracoronary Administration without Spillover to the Systemic Circulation Female Yorkshire white pigs (n=2) (27 kg) were sedated with telazol (100 mg, I.M.), intubated and shaved. An intravenous catheter was placed in a peripheral ear vein. The animals were moved to the surgery room, placed onto a support board, and secured to the surgical table with limb bindings. Animals were maintained anesthesized with isoflurane (2.5% in $O_2$) and their EKG monitored continuously throughout the procedure. Using a portable radiological source (GE STENOSCOP, GE Medical Systems USA) for fluoroscopic guidance, the left main coronary artery was intubated with a 6F guiding catheter JR 3.5 of 40 cm in length specially designed for the protocol (Cordynamic-Iberhospitex S.A. Barcelona, Spain). A baseline coronary angiography was performed.

In both animals, a coronary guide catheter of 2 mm diameter was advanced over a guide wire (Hi-Torque Balance Middle-Weight 0.014") to the origin of the left coronary artery. Through this catheter was advanced a microcatheter of 0.014" (0.3 mm) internal diameter and its tip positioned in the proximal portion of the left anterior coronary artery (LAD), just below the origin of the first perforating artery. This is the same location used to produce the experimental myocardial infarction and for the administration of the solution of growth factors described above. Another catheter was placed into the coronary sinus to collect cardiac venous blood samples during the procedure. Before starting the administration a peripheral, coronary venous and arterial blood sample was collected. In the case of abundant ventricular extra-systoles or ventricular fibrillation, Lidocaine of 1-3 mg/kg was administered intravenously. Pre-operative medication was administered as 75 mg clopidrogel (Plavix) and 250 mg aspirin one day before surgical procedure. Post-operative medication consisted of 75 mg clopidrogel (Plavix) and 125 mg aspirin daily until the sacrifice.

To determine the optimal size of the microspheres to be fully trapped in the capillary network a mixture of fluorescent polystyrene microspheres of diameters 2 μm, 4 μm, 6 μm, 10 μm; 12 μm and 15 μm, each labeled with a different dye (purchased from Invitrogen and from Polysciences Inc., Cat #F8830, F8858; F8824; Polybead Black dyed microsphere 6.0 μm, Megabead NIST 12.0 μm and F8842) were in mixed in a suspension of 20 mL of PBS at a concentration of $1\times10^6$ microspheres of each of the 6 sizes per mL and vortexed for 5 min to insure an homogeneous suspension. This suspension was administered at the origin of the left coronary artery of three pigs through the angiography catheter by a Harvard pump at a rate of 1 mL/min After administration of each mL (1 million microspheres) the injection was suspended for 3 min. during which time a coronary sinus blood sample was taken. Immediately after obtaining the blood samples, blood smear slides were prepared to check for the presence of fluorescent microparticles. After the complete administration of the 20 mL microsphere suspension coronary sinus blood samples were collected for an additional 3 hours at every 30 min intervals. At the conclusion of the experiment the animals were sacrificed and the heart excised, fixed and samples were taken for sectioning followed by histological and fluorescent microscopy examination.

Because the microspheres of different sizes were administered in equal numbers their ratios in the coronary sinus venous flow and in the myocardium should be mirror images of each other. Those particles that go through the capillary bed should have a high concentration in the coronary sinus blood and low in the myocardium at the end of the experiment. The reverse should be true for the particles that do not pass through the capillary bed. As shown below, only sizes ≤10 μm are efficiently retained in the myocardium but even microspheres of 10 and 12 μm leak through to a meaningful extent since between 19 and 8%, respectively of these microspheres passed into the systemic circulation. On the other hand, ≥1% of the 15 μm particles passed through the capillary bed and reached to coronary sinus.

TABLE 2

|  | Microsphere size in μm: | | | | | |
| --- | --- | --- | --- | --- | --- | --- |
|  | 2 | 4 | 6 | 10 | 12 | 15 |
| Outflow into coronary Sinus (calculated) in % | 95 | 73 | 53 | 19 | 8 | ≥1 |
| Retained in the myocardium 3 h after administration in % | ≤3 | 15 | 41 | 77 | 90 | ≥99 |

To determine whether the results shown above were specific for the myocardium or could be extended to other tissues, the same protocol was used to administer an identical suspension of microspheres through the femoral artery of the right leg. Blood samples were collected from the femoral vein and quadriceps muscle samples were analyzed to determine the permanence of the different microspheres in the skeletal muscle. The results are summarized in Table #3.

TABLE 3

|  | Microsphere size in μm: | | | | | |
| --- | --- | --- | --- | --- | --- | --- |
|  | 2 | 4 | 6 | 10 | 12 | 15 |
| Outflow into the venous return (calculated) in % | 92 | 67 | 59 | 12 | 11 | ≥1 |
| Retained in the skeletal Muscle 3 h post in % | ≤1 | 11 | 27 | 72 | 83 | ≥99 |

Conclusion:

The minimum size of microspheres that insures ≥99% retention in the tissue of interest is 15 μm in diameter. Because it is important to use the minimum effective size in order to minimize the production of micro foci of ischemia by obstructing precapillary arterioles, this diameter size is the optimal for the local delivery of substances to a particular tissue through its capillary bed.

Example 6

Administration of the Microspheres in the Coronary Circulation

A 20 mL suspension of fluorescent polystyrene microspheres of 15 μm (Invitrogen, Cat #F8842, FluoSpheres® polystyrene microspheres) at a concentration of $1\times10^6$/mL in PBS was prepared and vortexed for 5 min. This suspension was administered through the angiography catheter by a Harvard pump at a rate of 1 mL/min at the origin of the main left coronary artery. After administration of each mL (1 million microspheres) the injection was suspended for 3 min during which time a complete EKG and a coronary sinus blood sample was taken. Immediately after obtaining the blood samples, blood smear slides were prepared to check for the presence of fluorescent microparticles. The rest of the sample was saved for enzyme determinations. The procedure was continued until the electrocardiogram showed minimal alterations consistent with myocardial ischemia. Coronary blood flow (TIMI) was measured at the start of the experiment and after the administration of the particle suspension. The two pigs were allowed to recover, re-examined at 24 hours and sacrificed thereafter.

Results:

In animal #1 the first EKG alterations were detected after the administration of 16 mL of the suspension (16 million microspheres). In the second animal EKG alterations did not appear until after the administration of 18 mL (18 million microspheres). In both animals, the coronary blood flow was TIMI 3 (normal) at the end of the procedure. Animal #1 was sacrificed 24 hours after termination of the infusion. A complete EKG and blood samples were collected before sacrifice. The heart was processed for macroscopic and microscopic examination.

Animal #2 at 24 hours had a normal EKG and coronary blood flow (TIMI 3). After obtaining a set of blood samples the animal was sacrificed and the heart processed for macroscopic and microscopic examination.

All the blood smears from the samples taken from the coronary sinus and from the systemic circulation from animals #1 and #2 were examined by fluorescent microscopy at low and high magnification. No fluorescent beads were detected in any of the samples. This indicates that trapping in the capillary network of microspheres 15 μm in diameter is very efficient. Moreover, if there are any functional shunts from the coronary arteries to the right ventricle with this method of injection through the Thebesius veins, they are minor and not detected by the methods employed here.

The enzyme measurements (Table 4) show that animal #1 developed a small myocardial infarction as shown by the increased level of cardiac specific troponin T (TnT) in blood (values higher than 0.01 ng/ml are abnormal), while the values of animal #2 are normal and suggest that this animal developed only transient ischemia during the administration of the particles and recovered without any permanent myocardial damage. This interpretation was confirmed by the pathology as shown below. The macroscopic section of the heart of animal #1 shows microfoci of necrosis (pale areas) while the section of animal #2 is normal. This conclusion was confirmed by the histopathology (data not shown).

TABLE 4

| Marker | | PRE INJ CS | PRE INJ | POST CS | POST | POST 14 H | POST 24 H |
|---|---|---|---|---|---|---|---|
| PIG1 | CK | 574 | 669 | 423 | 567 | 1920 | 1982 |
|  | MB | 521 | 646 | 506 | 498 | 919 | 1231 |
|  | TrT | 0.01 | 0.01 | 0.01 | 0.01 | 1.72 | 1.35 |
| PIG2 | CK | 1120 | 1114 | 1099 | 1073 | 1834 | 1895 |
|  | MB | 922 | 791 | 920 | 523 | 867 | 739 |
|  | TrT | 0.02 | 0.01 | 0.04 | 0.01 | 0.01 | 0.01 |

Conclusion:

Administration of up to $15 \times 10^6$ microspheres 15 μm in diameter in the area irrigated by the left anterior descending artery (LAD) in a heart is well tolerated and does not produce myocardial damage. Doses above $15 \times 10^6$ microspheres have a high risk of producing small ischemic areas that might leave permanent scar. Therefore, with a loading in the mid-range of the values obtained with the PLGA as the polymer of 1 mg of protein per $1 \times 10^6$ microspheres of 15 μm diameter, it is possible to deliver up to 15 mg of the therapeutic agent to the capillary bed of the myocardium irrigated by the left coronary artery.

Example 7

Administration of PLGA Microbeads Loaded with Growth Factors

Once the safety dose range of 15 μm microspheres has bee determined, the same protocol was used to administer $10 \times 10^6$ PLGA microspheres (15 μm in diameter) to the same region of the myocardium. The microsphere suspension was composed of $4 \times 10^6$ PLGA microspheres loaded with a total of 2 μg of human recombinant insulin-like growth factor 1 (IGF-1); $4 \times 10^6$ PLGA microspheres loaded with a total of 1 μg of human recombinant hepatocyte growth factor (HGF). These two types of microspheres were also loaded with a fluorescent green dye in order to make easier their visualization in the blood and in the histological sections. In addition, the suspension contained $2 \times 10^6$ polystyrene fluorescent in the orange range from Invitrogen. The Invitrogen spheres were included to serve as control for the stability and distribution of the PLGA microspheres. The suspension in 10 mL of physiological PBS, was administered to the instrumented pigs as described above.

The administration of the suspension to the two animals was uneventful and there were no electrocardiographic signs of ischemia. The capillary blood flow was normal during and after the procedure (TIMI 3). One animal (pig #3) was sacrificed 30 min after the procedure and the other (pig #4) at 24 hours after the procedure. Both hearts were processed for macroscopic and microscopic analyses.

Neither the peripheral nor the coronary sinus blood samples of these two animals showed the presence to either Invitrogen or PLGA beads in the multiple blood smears. Preliminary analysis of lung, liver and spleen sections of these two animals also failed to detect the presence of either type of microspheres.

TABLE 5

| Marker | | PRE INJ CS | PRE INJ | POST CS | POST | POST 14 H | POST 24 H |
|---|---|---|---|---|---|---|---|
| PIG3 | CK | 589 | 692 | 432 | 657 | | |
|  | MB | 527 | 626 | 560 | 418 | | |
|  | TrT | 0.01 | 0.01 | 0.01 | 0.01 | | |

TABLE 5-continued

| Marker | | PRE INJ CS | PRE INJ | POST CS | POST | POST 14 H | POST 24 H |
|---|---|---|---|---|---|---|---|
| PIG4 | CK | 467 | 468 | 441 | 442 | | 434 |
|  | MB | 451 | 505 | 562 | 378 | | 411 |
|  | TrT | 0.01 | 0.01 | 0.01 | 0.01 | | 0.01 |

Legend for Tables 4 and 5.

Markers: CK, creatine kinase; MB, the MB isoform of creatine kinase which is cardiac specific; TrT, Cardiac troponin T, which is the most specific and sensitive marker for myocardial damage. PRE INJ CS, blood sample taken from the coronary sinus at the start of the procedure; PRE INJ, systemic blood sample taken at the start of the procedure; POST CS, blood sample taken from the coronary sinus at the end of the procedure; POST, blood sample from systemic circulation taken at the end of the procedure; POST 14H, systemic blood sample taken at 14 hours after the procedure; POST 24H, systemic blood sample taken 24 hours after the procedure before sacrificing the animal.

The macroscopic sections of these two animals were completely normal (not shown). The analysis of the section of pig #3 under the fluorescent microscope showed the distribution of the PLGA beads (green) and the polystyrene beads (red/orange) in the capillary vessels in the approximate ratio of 1:4 (FIG. 10 below), as would be expected from the composition of the mixture administered. There was no evidence of any microscopic tissue damage in any of the regions of the heart examined. In pig #4 the number of PLGA beads (green) has already decreased significantly and the ratio of these beads to the polystyrene ones (red/orange) is closer to 1:1 (see FIG. 11), indicating that the PLGA beads become degraded with a half life of ~16 hours.

Effectiveness of IGF-1 and HGF Administered in Microspheres to Stimulate the Resident Cardiac Stem Cells As described above, the combination of IGF-1 and HGF administered through the coronary arteries was very effective in stimulating the activation of the resident cardiac stem cells. In this preliminary assay we monitored the activation of the stem cells in the region were the microspheres were delivered and compared it to a region of the left ventricle not irrigated by the left coronary artery. As can be seen in the images in FIG. 11, most resident stem cells in the non-treated myocardium are quiescent (highlighted by arrows/arrow heads) while those of the treated region have entered into the cell cycle, as demonstrated by the expression of the cell cycle marker ki-67 (yellow signal in the nucleus—in Figures the light "spots" in the highlight areas). Therefore, administration of growth factors on a solid substrate that delivers them to the capillaries and keep them there until they have unloaded into the surrounding interstitial space, is an effective method of growth factor administration for the stimulation of the endogenous stem cell population.

Conclusion:

Local delivery of IGF-1 and HGF to particular regions of the myocardium by mean of biodegradable microbeads of a diameter which does not allow they to cross the capillaries and enter the systemic circulation is effective in stimulation the resident stem cells of particular regions of the tissue without affecting those not targeted by the therapy.

Example 8

Porcine c-Kit$^{pos}$ Cardiac Stem and Progenitor Cells are Multipotent and Phenotypically Similar to Those of Other Animal Species Histological sections of myocardium from 3 Yorkshire pigs weighing 24±3 kg were examined by confocal microscopy for the presence of cells positive for the common stem cell marker, c-kit, the receptor for stem cell factor (SCF), known to be expressed by the majority of CSCs. Small cells positive for c-kit (c-kit$^{pos}$) were distributed throughout the atrial and ventricular myocardium (FIG. 1A-B) with a higher density in the atria (no difference between left and right atria, data not shown) and the ventricular apex, compared to other cardiac regions (FIG. 1C). This distribution pattern matches the anatomical location of the c-kit$^{pos}$ CSCs in the hearts of other animal species, including humans. Accordingly, the density of c-kit$^{pos}$ cells in the pig heart is similar to human and rodent myocardium: 1 cell per ~1,000 myocytes or ~50,000 c-kit$^{pos}$ cells per gram of tissue.

Myocardial tissue samples from different porcine cardiac regions were enzymatically digested to obtain a myocyte-depleted cell population. c-kit$^{pos}$ cells constituted 10±3%, 3±2% and 7±3% of the starting myocyte-depleted cardiac cell population from the atria, ventricle, and apex, respectively (FIG. 1D).

The c-kit$^{pos}$ cells were separated using MACS technology (21) which yielded a highly enriched cell preparation constituted by >90% of c-kit$^{pos}$ cells (FIG. 1E). FACS analysis showed that the c-kit$^{pos}$ enriched cardiac cells were negative for the pan leukocyte marker CD45 and the endothelial/hematopoietic progenitor marker CD34 (FIG. 1E). A high fraction (87%) of c-kit$^{pos}$ porcine cardiac cells expressed CD90, (a common non-specific mesenchymal marker) and CD166 (adhesion molecule) (FIG. 1E). Only a small fraction was positive for the markers of hematopoietic/endothelial progenitors, CD105 and CD133 (Suppl FIG. 1). c-kit$^{pos}$ cardiac cells were negative when analyzed for a panel of CD markers specific for other hematopoietic, mesenchymal and endothelial cell lineages, including CD13, CD14, CD31, CD38, CD44, CD33. From these analyses we can conclude that the porcine c-kit-sorted cardiac cells are c-kit$^{pos}$, CD90$^{pos}$, CD166$^{pos}$, CD105$^{low}$, CD133$^{low}$ and CD45$^{neg}$, CD34$^{neg}$, CD31$^{neg}$, CD44$^{neg}$.

Figures 2A, 2B, 2C, 2D, 2E, 2F, 2G, 2H:
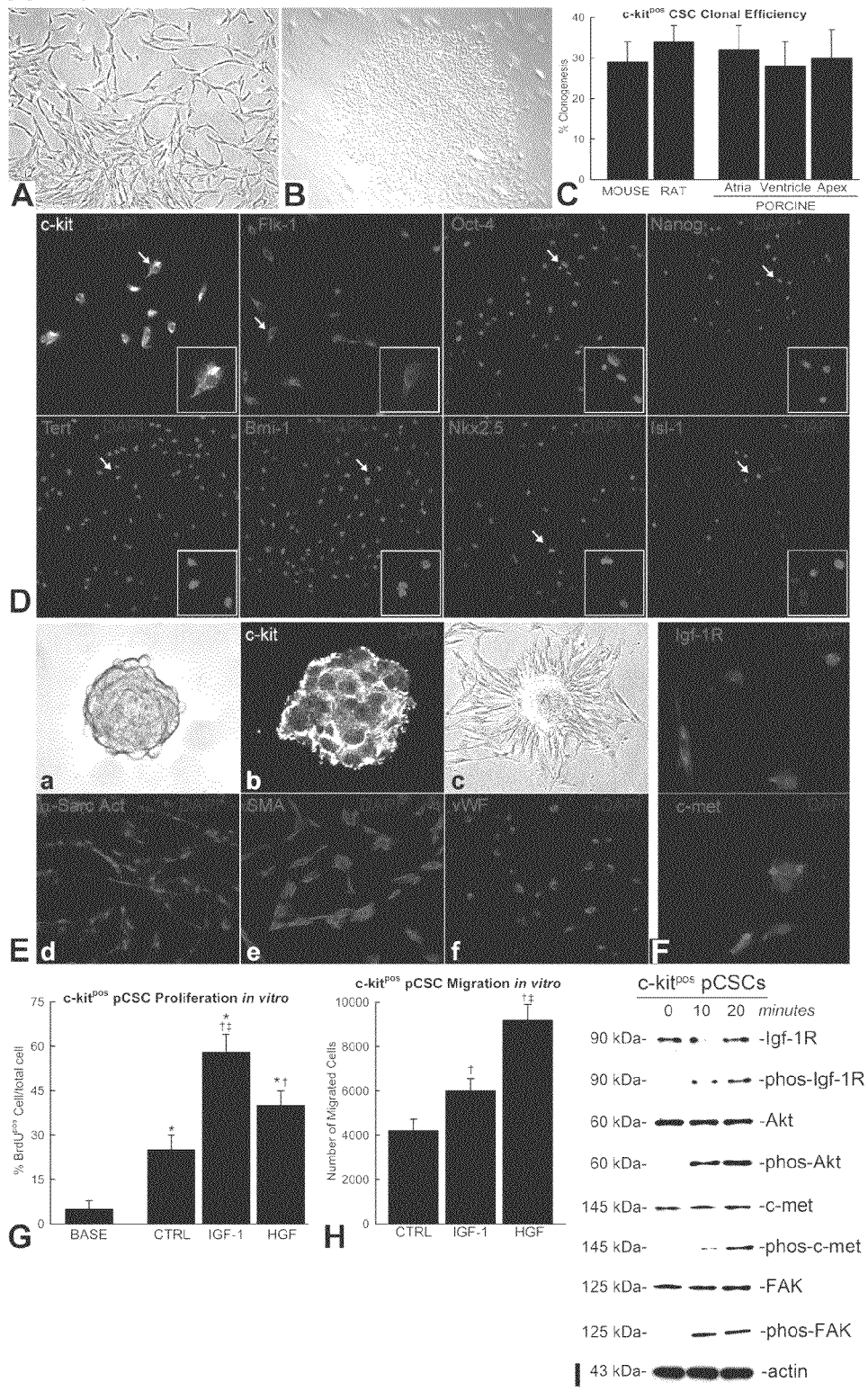
FIGS. 2A-2H show light microscopy images showing various expanded porcine cardiac cells.

Freshly isolated c-kit$^{pos}$ cardiac cells from atria, ventricles and apex were expanded in culture (4 passages) and then deposited as a single cells into 96-well Terasaki plates to generate single cell clones (FIG. 2A-B). The clonal efficiency of the porcine cells was similar for all cardiac locations and to the previously reported cloning efficiency of the rodent CSCs (FIG. 2C) (Beltrami et al. Cell 2003). We randomly picked 2 clones each from atria, ventricle and apex-derived cells and further expanded them. These clones showed a ~30 hours doubling time and have been propagated so far for more than 65 passages and serially sub-cloned every 10 passages, without reaching growth arrest or senescence. These c-kit$^{pos}$ cardiac cell clones have maintained a normal karyotype without detectable chromosomal alterations.

Cloned c-kit$^{pos}$ porcine cardiac cells were analyzed for markers of stemness and cardiac-lineage commitment using immunocytochemistry. Cells showed positivity for c-kit (90±8%), Flk-1 (86±9%), Oct3/4 (62±11%), Nanog (46±5%), telomerase (81±10%), Bmi-1 (70±14%), NRx2.5 (52±8%), Is1-1 (8±6%) (FIG. 2D). Because the clones originated from single cells, the wide expression of the multipotency genes in their progeny suggested that the level of expression of these genes in the parental cell population is very high. Unfortunately, the primary population of c-kit$^{pos}$ cells is a mixture of CSCs, progenitors and precursors and we do yet have markers specific for the 'real' CSCs. Therefore, it is only possible to infer the phenotype of these cells through the analysis of their descendants.

When cloned c-kit$^{pos}$ porcine cardiac cells were plated in modified cardiosphere formation medium (mCSFM) in bacteriological dishes (Corning), they grew in suspension and generated spherical clones, named cardiospheres (FIG. 2E) (Beltrami, A. P. et al., 2003. Cell 114:763; Oh H, Bradfute S B, Gallardo T D et al. Cardiac progenitor cells from adult myocardium: homing, differentiation, and fusion after infarction. Proc Natl Acad Sci USA 2003; 100(21):12313-12318; Matsuura K, Nagai T, Nishigaki N et al. Adult cardiac Sca-1-positive cells differentiate into beating cardiomyocytes. J Biol Chem 2004; 279(12):11384-11391). When cardiospheres were placed in laminin-coated plastic dishes with cardiogenic differentiation medium, they attached and cells spread out from the sphere acquiring a flat morphology (FIG. 2E). Four to six days after plating, these peripheral flat cells expressed proteins specific for myocyte (27±4%), endothelial (10±6%) and smooth muscle cell (34±5%) lineages (FIG. 2E). These results show that porcine c-kit$^{pos}$ cardiac cells have true stem cell characteristics, i.e. they express markers of sternness, are clonogenic, self-renewing, and multipotent. Thus, porcine c-kit$^{pos}$ cardiac stem cells (hereafter identified as pCSCs) have a pattern of gene expression and a phenotype consistent with c-kit$^{pos}$ CSCs isolated from other species (Ellison et al., 2007. J. Biol. Chem. 282:11397).

Porcine CSCs Express Intact IGF-1, HGF and SCF Signaling Pathways that Modulate Their Activation The results show the presence of true pCSCs in the porcine heart.

pCSCs express IGF-1 and c-met receptors in vivo and in vitro (FIG. 2F). When grown in culture, freshly isolated pCSCs respond to the stimulation by hrIGF-1, hrHGF and hrSCF with cell proliferation (FIG. 2G) and migration (FIG. 2H). Upon ligand binding, specific downstream effector pathways were activated in pCSCs (FIG. 2I). Similar results were obtained with cells from the expanded single cell clones (data not shown). Therefore, pCSCs have functionally coupled GF receptor systems that can be exploited in vivo to test myocardial regeneration protocols.

Example 9

Production of Myocardial Infarction in Pigs, Monitoring of Ventricular Function and Myocardial Regeneration by In Situ by Stimulation of Resident Cardiac Stem Cells with Growth Factors All animal studies were approved by proper committees of Escuela Veterinaria y Hospital de León, León, Spain. Female Yorkshire white pigs (n=26) (27±3 kg) were sedated with telazol (100 mg, I.M.), intubated and shaved. An intravenous catheter was placed in a peripheral ear vein. The animals were moved to the surgery room, placed onto a support board, and secured to the surgical table with limb bindings. Animals were maintained anesthesized with isoflurane (2.5% in $O_2$). In all 26 animals, a coronary balloon catheter was advanced over a guide wire and positioned in the proximal portion of the left anterior coronary artery (LAD), below the origin of the first perforating artery. Pigs were given 125UI/kg of heparin before the infarction was induced and then heparin infusion (10UI/kg/h) during the infarction procedure. To induce infarction, the LAD coronary artery was occluded by balloon inflation (2.5 mm diameter) for 75 mins. For anti-arrhythmic medication, pigs were continuously infused throughout the procedure with Amiodarona (Trangorex) (5 mg/kg/h) beginning 15 minutes before the infarction. In the case of abundant ventricular extra-systoles or ventricular fibrillation, Lidocaine of 1-3 mg/kg was administered intravenously. Preoperative medication was administered as 75 mg clopidrogel (Plavix) and 250 mg aspirin one day before surgical procedure. Post-operative medication consisted of 75 mg clopidrogel (Plavix) and 125 mg aspirin daily until the sacrifice.

Human recombinant IGF-1 and HGF (Peprotech) were administered in differential doses (ranging from 2 μg to 8 μg of IGF-1 and from 0.5 μg to 2 μg of HGF) to 17 pigs through a perfusion balloon catheter advanced immediately distal to the origin of the first septal artery 30 minutes after coronary reperfusion. The GFs were administered in 15 ml of PBS at a rate of 2.5 ml per minute with a 2 min reperfusion after every 5 ml administration. Saline alone was injected in another 9 pigs with MI (saline-placebo control group; CTRL) using the same protocol. Five (2 in the CTRL group and 3 in the GF groups) of the 26 animals died during acute myocardial infarction (AMI) (acute mortality of ~30%). Subsequently, 3 animals died in the postoperative period: one animal on day 1 (CTRL group), one animal on day 13 (CTRL group) and one animal on day 14 (GF group). Of the remaining 18 pigs completing the study protocol, 13 were in the GF-treated groups and 5 in the CTRL group. Specifically, of the surviving 18 GF-treated animals, 4 received a 1× dose of the GFs (2 μg IGF-1 and 0.5 μg HGF; GF-1x), 5 animals received a 2× dose (4 μg IGF-1 and 1 μg HGF; GF-2x) and 4 animals received a 4× dose (8 μm of IGF-1 and 2 μm of HGF GF-4x)). Directly after the GFs or saline alone administration, all surviving animals were implanted with an osmotic pump loaded with 10 ml of a 0.5 M solution of BrdU for the duration of the study. Pigs were sacrificed at 21 days after MI and growth factor administration. The group to which each pig belonged was kept blind for investigators carrying out the immunohistochemical analysis.

Cardiac Function Measurements.

Cardiac function was measured by echocardiography at baseline, immediately after coronary occlusion and before sacrifice. Briefly, parasternal long- and short-axis views were obtained with both M-mode and 2-dimensional echo images. LV dimensions (LVEDD and LVESD) were measured perpendicular to the long axis of the ventricle at the midchordal level. LV ejection fraction and radial strain were calculated. Local intracoronary IGF-1/HGF Injection Preserves the Organization of the Infarcted Tissue and Improves Cardiomyocyte Survival after Acute Myocardial Infarction Human recombinant IGF-1 and HGF (hereafter abbreviated as IGF-1/HGF or GFs) were administered in differential doses to pigs by intracoronary injection 30 minutes after acute myocardial infarction. Additional pigs were injected with identical volume of saline alone, constituting the control group (CTRL).

The infarct size, as determined by planimetry, as a percent of the coronal circumferential area was not different between the GF-treated and CTRL group (28±5%, 26±7%, 29±5% in GF-1x, -2x and -4x, respectively, vs. 27±4% in CTRL).

Figures 3A, 3B, 3C, 3D, 3E, 3F, 3G, 3H, 3I:
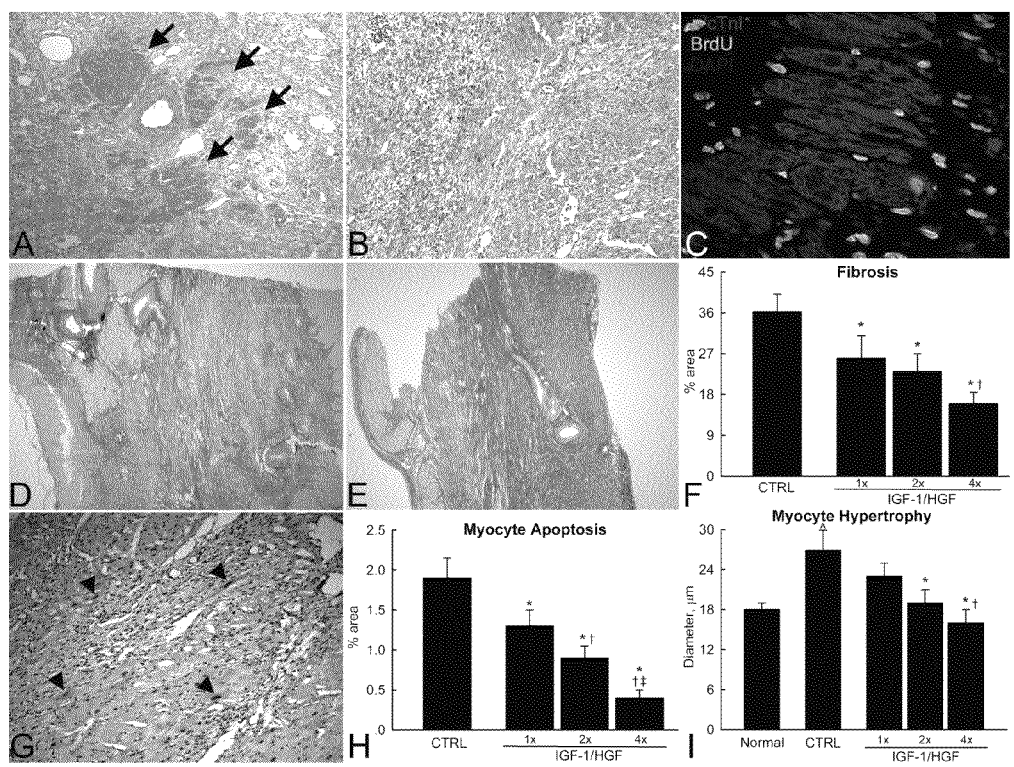
FIGS. 3A-3I show H&E staining of GF-treated porcine hearts.

H&E and Sirius Red stained cross sections of the cardiac tissue in the remote, border and infarct zone revealed islands of survived myocardial tissue distributed amongst the fibrotic scar tissue in the infarct zone. These survived myocardial islands were much more abundant in the infarcted area of the GF-treated myocardium than in the CTRL-treated animals (FIG. 3A-B). Double immunofluorescence staining for α-sarcomeric actin and BrdU of the sections analyzed by confocal microscopy revealed that these islands consisted mainly of large α-sarcomeric actin positive, BrdU negative cardiomyocytes, a phenotype that confirmed their survival as pre-infarct myocardium and their mature, even hypertrophic nature (FIG. 3C). Furthermore, the GF-treated pig hearts had significantly less fibrotic tissue in the infarct region, compared to CTRL (FIG. 3D-F). More interestingly, this decrease exhibited a positive linear relationship with the dose of GF administered (FIG. 3F).

The study was not specifically geared to monitor the effect of the GF therapy on early cell death. However, from the results presented hereafter, it is clear that myocyte death continues to be very high in the peri-infarct/border zone a long time after the coronary occlusion/reperfusion event. This is likely due to the effects of pathological remodeling, which is known to establish a vicious circle between morphological adaptation and continued cell death. As shown in FIG. 3G-H, IGF-1/HGF administration significantly reduced late myocyte death in a dose dependent manner, as shown by a decrease in the number of myocytes positive for activated caspase-3, compared to CTRL. Consistent with the preservation of the anatomic morphology, myocyte survival and decreased remodeling, the GF-treated hearts exhibited a decreased myocyte hypertrophic response when compared to CTRL (FIG. 3I). Taken together these findings indicate that IGF-1/HGF administration after acute MI has an important effect in preserving cardiomyocyte number and myocardial wall structure, reducing load on the surviving myocytes, which results in improved myocardial remodeling and decreased stimulus for myocyte death and hypertrophy of the surviving myocardium.

Figures 4A, 4B, 4C, 4D, 4E, 4F, 4G, 4H, 4I:
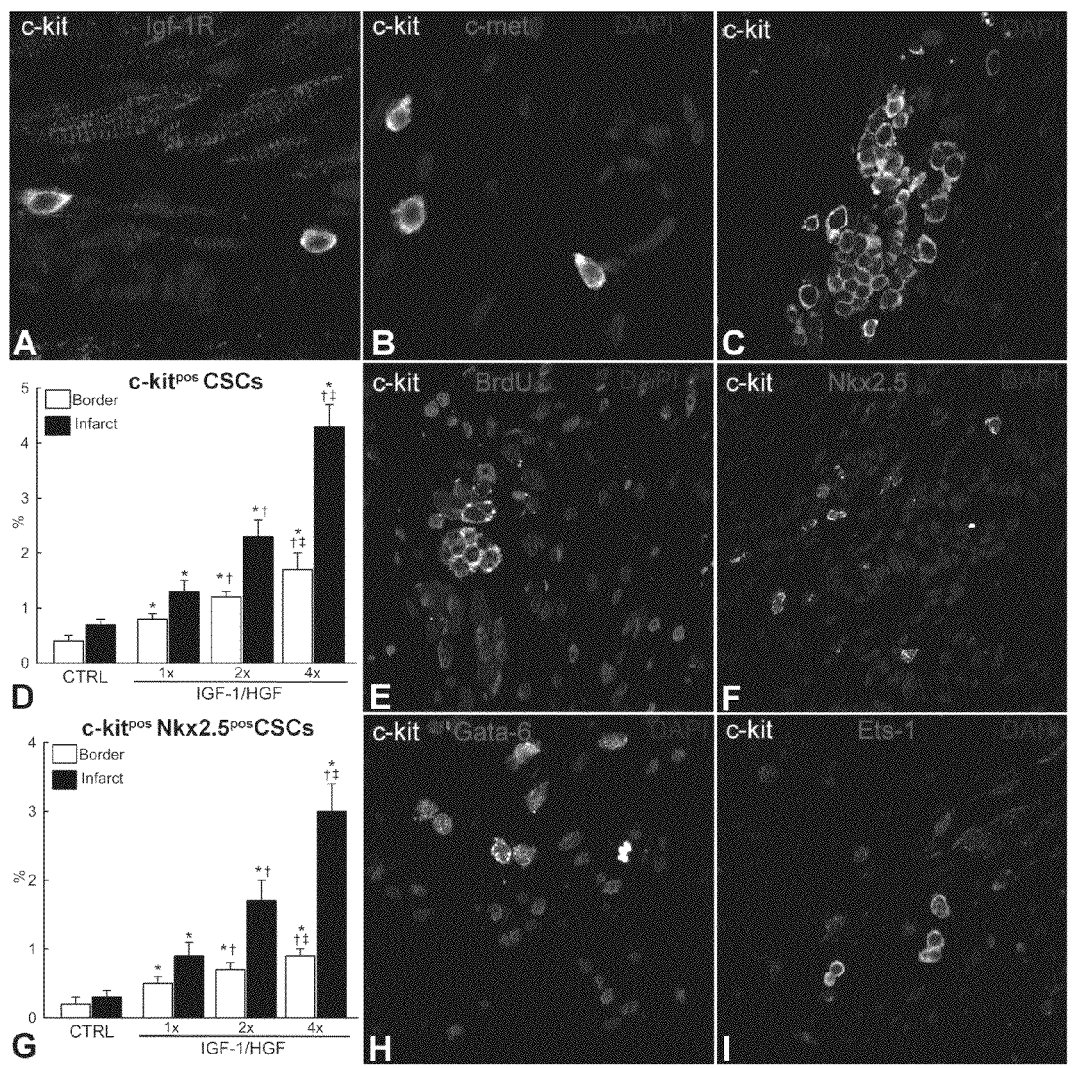
FIGS. 4A-4I show evidence of activation of endogenous CSCs.

Intracoronary Administration of IGF-1/HGF After Acute Myocardial Infarction Activates the Resident pCSCs In normal (not shown) and post-MI hearts, ~90% c-kit$^{pos}$ pCSCs in situ express IGF-1 and c-met (HGF) receptors as detected in by immunohistochemistry (FIG. 4A-B). Accordingly, the GF-treated infarcted pig hearts show a significant increase in the number of c-kit$^{pos}$ pCSCs in the border region and even higher in the infarcted area, 21 days after MI (FIG. 4C-D). That this increase in c-kit$^{pos}$ pCSCs is the result of GF administration is confirmed by its direct correlation to the GF-dose administered (FIG. 4D). At the highest GF dose, the number of c-kit$^{pos}$ pCSCs in the infarcted area is >6-fold higher than in the CTRL hearts (FIG. 4D, SupplTable). Moreover, the linear increase between the 1× and the 4× doses indicates that we have not reached a saturating dose to produce the maximum regenerative response. Many of the pCSCs were BrdU positive, a fixture that documents their birth after the production of the MI (FIG. 4E). Their cycling nature was confirmed by Ki-67 staining, which marks cells that are or have recently been in the cell cycle (data not shown). Many c-kit$^{pos}$ cells expressed the transcription factors Nkx-2.5, Ets-1 or Gata6 indicative of their differentiation toward the main cardiac lineages, i.e. myocyte, endothelial and smooth muscle cells (FIG. 4F-I). Quantitative analysis revealed that the number of c-kit$^{pos}$ NRx2.5$^{pos}$ cells (committed myocyte/vascular precursors), significantly increased in the infarct and border regions in GF-treated pig hearts in a GF-dose dependent manner (FIG. 4G), reaching levels which were >10-fold higher than in CTRL hearts.

Figures 5A, 5B, 5C, 5D, 5E, 5F, 5G, 5H, 5I:
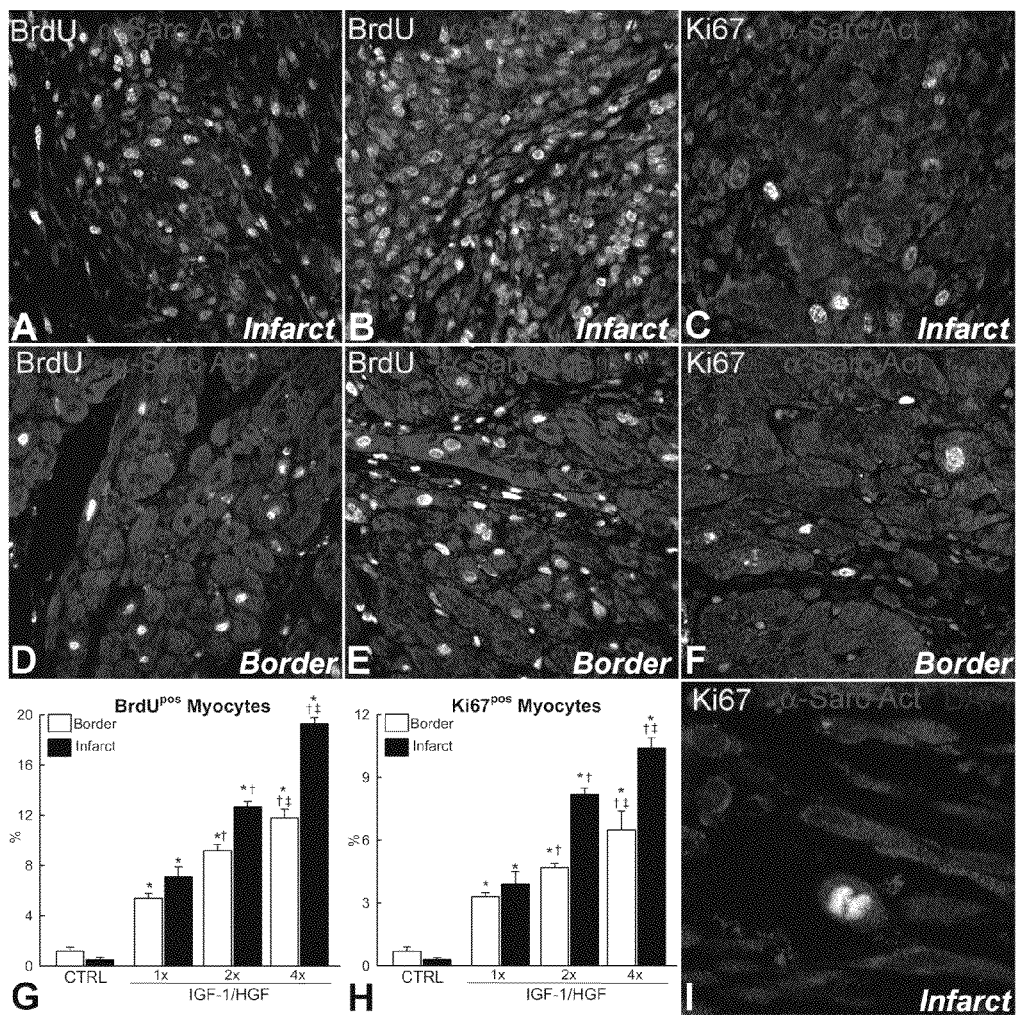
FIGS. 5A-5I show regenerating bands of small, newly formed cells.

IGF-1/HGF Treatment Produces Robust Myocardial Regeneration after Acute Myocardial Infarction The GF-treated hearts, both in the infarct and peri-infarct/border regions, harbored a large population of very small, newly formed BrdU$^{pos}$ myocytes that had not yet reached the terminally differentiated state (FIG. 5). These data were confirmed by the expression of Ki67 in the small newly formed myocytes (FIGS. 5C and F), some of which were in mitosis and cytokinesis, confirming their immature nature (FIG. 5I). Newly formed BrdU$^{pos}$ myocytes were also present in the peri-infarct/border region of the untreated saline-injected CTRL pigs. However, their number was ~1/10 of the treated hearts and they were practically absent in the infarct zone (FIG. 5).

As it was the case for the pCSCs, there was a direct correlation between the number of small BrdU$^{pos}$/Ki67$^{pos}$ newly formed myocytes with GF-dose, both in the infarct and border regions (FIG. 5G-H). In the GF-treated myocardium, the small BrdU$^{pos}$ myocytes were organized as clusters of regenerating bands in the infarct zone. These regenerating bands were more organized in structure, and more compact and dense with increasing GF dose (FIG. 5A-B). Finally, neither the number nor the appearance of newly formed myocytes (the BrdU$^{pos}$ or Ki67$^{pos}$ in the distal region from the infarct (the spared myocardium) was not significantly different between GF-treated and CTRL animals (data not shown).

Figures 6A, 6B, 6C, 6D, 6E, 6F, 6G, 6H, 6I:
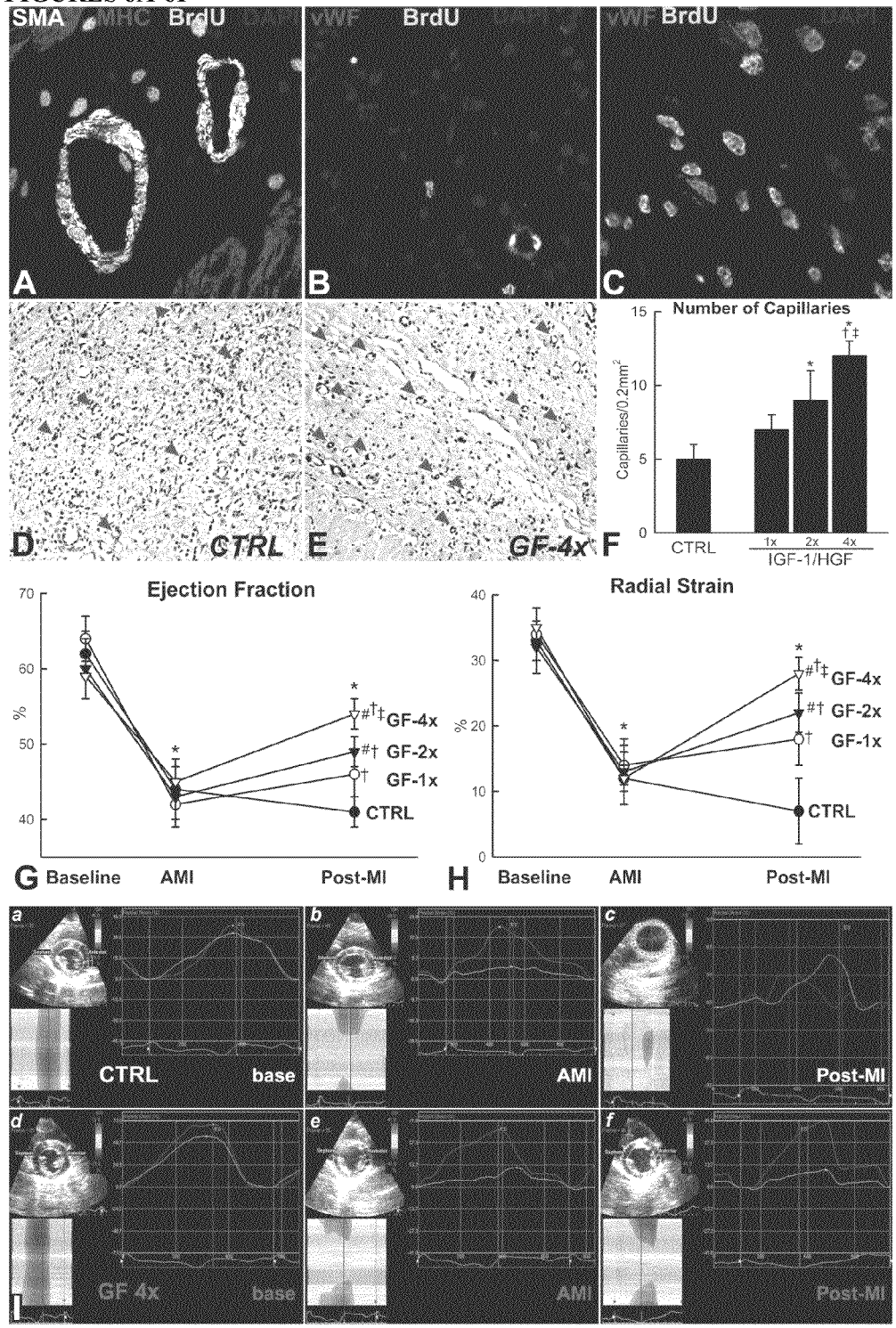
FIGS. 6A-6I show various images of newly formed tissue.

Newly formed BrdU-positive vascular structures were also evident in the border and infarcted myocardium (FIG. 6A-C). GF-treated hearts displayed increased number of capillaries and arterioles in the infarct zone, compared to saline-treated CTRL and this response was dose dependent (FIG. 6D-F). Interestingly, new micro-vessels were most evident surrounding the survived islands of myocardium within the infarcted zone mentioned above which also had a higher density of newly formed small BrdU$^{pos}$ myocytes and regenerating bands (Gandia, C. et al., 2008. Stem Cells 26:638). This organization suggests the production of cardiopoietic (Behfar, A. et al., 2007. J. Exp. Med. 2007 204: 208) factors by the adult spared myocytes acting on the pCSCs.

The regenerated myocytes in the infarct zone at 21 days after MI were immature as demonstrated by their average size, as well as by the fact the many of them were still cycling as demonstrated by the expression of Ki-67 (FIG. 5I F). In agreement with the suggested role for the cardiopoietic role of the mature myocytes, newly formed myocytes in contact or close proximity with mature ones (i.e. in the border zone) are of significantly larger size than those in the middle of the scar with no proximity to spared tissue (FIG. 5). It is also evident that GF-treatment plays a role in myocyte maturation as shown by the increased average myocyte size with increased GF dose.

Given the size of the porcine heart and the volume of the infarcted area, it is not possible to determine with any accuracy either the number of myocytes lost or the number of myocytes regenerated by the GF treatment. Nevertheless, careful sampling of the infarcted zone and the peri-infarct/border areas leaves no doubt that at 28 days the GF-treated infarcted heart has regenerated most of the lost myocytes, if not all.

Example 10

Intracoronary GF Administration Preserves and Might Improve Ventricular Function Echocardiographic imaging showed that left ventricular ejection fraction (LVEF) was significantly depressed in CTRL and GF-treated pigs following coronary occlusion (FIG. 6G). However, 28 days after AMI, LVEF worsened slightly in CTRL, while it was significantly preserved/improved by the GF-treatment, when compared to CTRL (FIG. 6G). In order to gain further insight in regional cardiac function, tissue Doppler echocardiography was employed to measure antero-septal radial strain that was significantly improved in GF-treated pigs, compared to CTRL (FIG. 6H-I). Cardiac function preservation/improvement correlated with increasing GF dose (FIG. 6).

Example 11

Intracoronary Administration of Up to 50 µg of IGF-1 Encapsulated in 15 µm Diameter PLGA Microspheres does not Spill Over into the Systemic Circulation As demonstrated by Example #5, ≥99% of the 15 µm diameter microspheres are trapped into the capillary network of the target tissue, and specifically the myocardium. These data, however, do not address the issue of whether when the active molecule is unloaded is retained within the tissue or whether it leaches out into the capillary circulation and the venous return. To explore this issue, 5×10$^6$ microspheres loaded with a total of 50 µg of rhIGF-1 were administered intracoronary at the origin of the left anterior descending artery following the same administration protocol outlined in Examples #5-7. The main different was that a catheter was left into the coronary sinus throught the jugular vein. During the administration, three hours after the procedure and then every 12 hours for the next 3 days blood samples were collected from the coronary sinus and the venus blood through an ear vein. Serum was prepared and the samples frozen in LN2 until the completion of the collection. All the samples were analyzed by ELISA employing human IGF-1 detection kit (R&D, Minneapolis, Minn., USA) which does not cross-react with the porcine IGF-1. None of the samples either from the coronary sinus or from the systemic venous return scored positive. In our hands the minimal detection limits of the assay were 52.5 ng/ml for IGF-1. Therefore, although it is possible that some leakage below the detection levels of the ELISA occurred, it is clear that the majority of the IGF-1 never left the myocardium.

Example 12

Intra-Arterial Local Administration of IGF-1/HGF to Damaged Skeletal Muscle Induced the Activation of the Muscle Stem Cells and Stimulates Regeneration To test whether the protocol used to treat the damaged myocardium was effective in the treatment of other tissues, the same protocol was used to treat the post-ischemic skeletal muscle of the right leg of 3 pigs in which ischemic damaged had been produced by a 45 min complete balloon occlusion of the femoral artery. As in the case of the myocardium, after a 30 min reperfusion by deflation of the balloon, a suspension of 20 mL of PBS containing IGF-1 and HGF microspheres of 15 µm diameter, prepared as described in example #2 for a total dosis de 8 µm of IGF-1 and 2 µm of HGF. The animals were sacrificed 3 weeks later and biopsies of the quadriceps muscle analyzed by immunohistology to determine the degree of activation of the stem cells in the lesion.

As described for the myocardium, after the occlusion of the femoral artery the animals were implanted an osmotic pump to continuously deliver a solution of BrdU known to efficiently label all replicating cells. In this manner all cells born after the start of the therapy are BrdU label, which allows for a comparison of the regenerative reaction between the controls and the treated animals. In each case the quadriceps of the left leg served as undamged control.

Figures 12A, 12B, 12C, 12D:
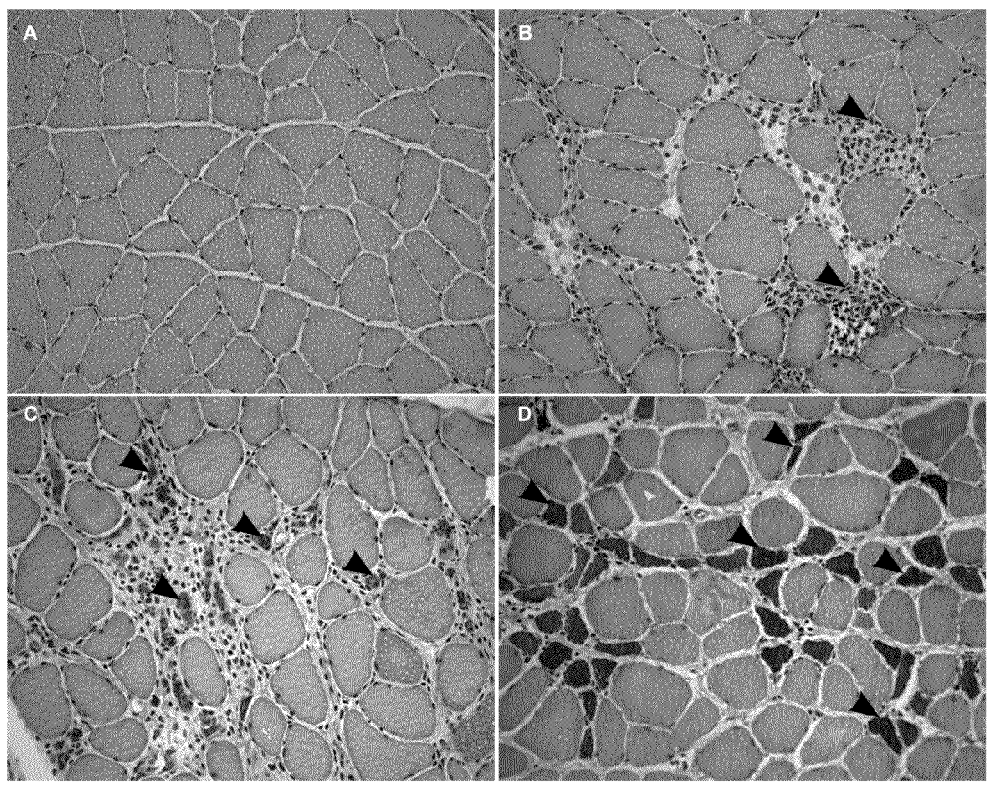
FIGS. 12A-12D are micrographs and show histological images of control and damaged quadriceps muscle.

As shown in FIG. 12, and Table 6, the local administration of IGF-1/HGF encapsulated in PLGA microspheres of 15 µm in diameter was very effective in stimulation the regeneration of muscle tissue in the treated leg but not in the contralateral one as compared with the ischemic but placebo treated controls.

TABLE 6

Skeletal Muscle Regeneration in Response to Local Administration of Growth Factors
# of BrdU labeled myofiber nuclei per 1 × 10³ myofiber nuclei

| Animal # | Damaged leg | Contralateral leg |
|---|---|---|
| 1 | 337 | 17 |
| 2 | 289 | 22 |
| 3 | 364 | 13 |

Conclusion:

The local administration of growth factors to damaged tissue others than the myocardium has a stimulatory effect o in the regenerative reaction of the damaged tissue which is localized to the area downstream from the site of administration of the microspheres, as is expected for a delivery system that targets the capillary network of the damaged tissue/organ.

Example 13

Intracoronary Injection of IGF-1/HGF/SCF has a More Potent Effect in the Activation of the CSCs and Preserving Ventricular Function than IGF-1/HFG Alone To test whether the addition of new factors to the protocol described in the previous Examples would improve the regenerative reaction of the post-infarcted myocardium, a group of 3 animals were administered the higher doses of IGF-1 (8 µg) and HGF (2 µg) used in example #9 together with 4 µg of SCF. Each of these factors was encapsulated in PLGA microspheres of 15 µm diameter as described in Example #2. The protocol for the production of the infarct, monitoring and the administration of the microsphere suspensions was as described in Examples #5-7. The animals were sacrificed at 4 weeks after the treatment.

Figure 13A:
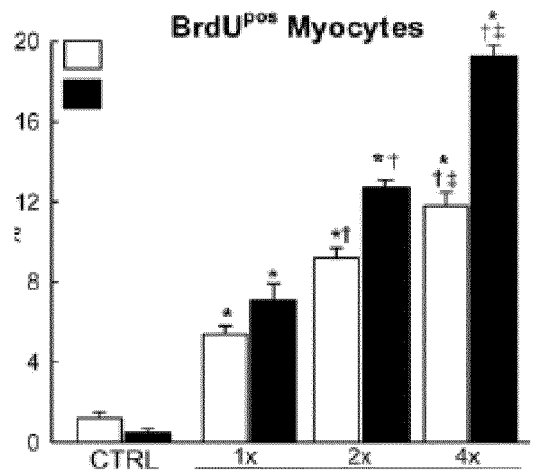
FIG. 13A compares the effect in the number of regenerated cardiac myocytes in pigs post-AMI treated with a combination of two types of microspheres.
Figure 13B:
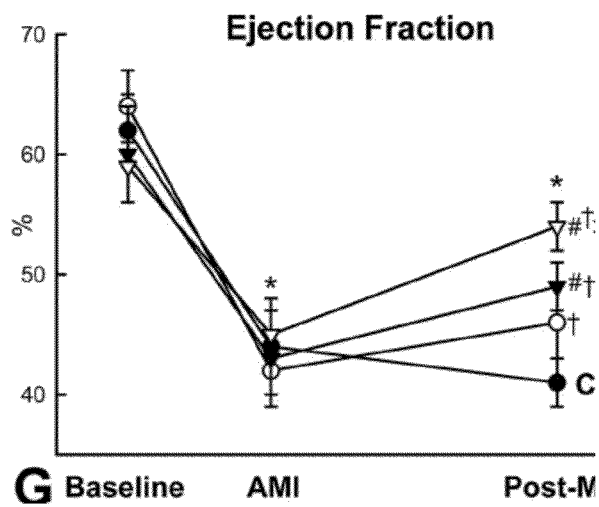
FIG. 13B shows the left ventricle ejection fraction prior to, immediately after and 4 weeks post-AMI as determined by echocardiography of the pigs treated with different combinations of microspheres.

As shown in FIG. 13A and FIG. 13B, the regeneration produced by the three factors protocols is significantly better in both the level of regeneration as well as in the maturation of the regenerated myocytes that by the combination of IGF-1/HGF. It is reasonable to extrapolate from these data that in addition to the addition or subtraction of particles with particular factors, other variations might involve changing the dose of a particular factor or set of factors, the profile of release/unloading for a particular factor, the degree of loading, etc.

Conclusion:

The present invention allows for the formulation of an almost infinity number of specific combination of therapeutic compounds starting from a limited set of building blocks in which each factor can be used at different doses, different patterns of release and combined with an unlimited of other factors. This allows in a single administration to target a particular tissue with different combinations of therapeutic agents each of which might act at a different time, on a different cell target, and require a different effective dose. These possibilities are particularly advantageous for tissues of difficult access which can not be accessed repeatedly, such as the myocardium and most of the internal organs.

FIGURE LEGENDS

FIG. 1. Distribution and Characterization of c-kit$^{pos}$ Cardiac Cells in the Adult Pig Heart.

(A-B) Representative confocal images of c-kit positive (c-kit$^{pos}$; white) cells in the right atria (A) and left ventricle (B) of the normal pig heart. Cardiomyocytes stained in red (shown in grey in the figures) by α-sarcomeric actin (α-sarc act) and nuclei stained with DAPI in blue. (C) c-kit$^{pos}$ cells are distributed throughout the atrial and ventricular myocardium with a higher density in the atria and the apex, compared to Right and left ventricle (RV, LV). *p<0.05 vs RV and LV. (D) Representative FACS analysis of c-kit$^{pos}$ cells within the myocyte-depleted cardiac cell population for the atria, ventricle (RV), and apex. (E) c-kit$^{pos}$ cells obtained using MACS show >90% enrichment. FACS analysis of c-kit$^{pos}$ enriched porcine cardiac cells revealed that they are negative for hematopoietic cell lineage markers CD45 and CD34. Also, a high fraction of c-kit$^{pos}$ porcine cardiac cells express the mesenchymal cell lineage markers, CD90 and CD166.

FIG. 2 c-kit$^{pos}$ Porcine Cardiac Cells Express Sternness Markers, have Stem Cell Properties of Clonogenicity, Self-Renewal, Cardiosphere-Forming and Multipotency, and Express Intact Signaling IGF-1/HGF Systems Modulating their Activation.

(A) A light microscopy image showing expanded c-kit$^{pos}$ porcine cardiac cells at the 4$^{th}$ passage. (B) A light microscopy image of a clone, after single c-kit$^{pos}$ porcine cardiac cells were deposited into wells of terasaki plates to generate single cell clones. (C) The clonogenicity of c-kit$^{pos}$ porcine cardiac cells was similar across cardiac chambers, and compared to mouse and rodent CSCs. (D) Immunofluorescent staining of cloned c-kit$^{pos}$ porcine cardiac cells confirmed the expression of c-kit (white), and revealed the expression of Flk-1, Oct-4, Nanog, Tert, Bmi-1, NRx2.5 and Is1-1 (all shown in grey), which indicates they are a mixture of cardiac stem and progenitor cells. Images are 20× magnification, with zoom captures as inset. (E) Cloned c-kit$^{pos}$ porcine cardiac cells formed cardiospheres (a). When c-kit$^{pos}$ (white) cardiospheres (b) were placed in laminin-coated dishes in cardiogenic medium, cardiosphere cells spread out from the sphere (c). Four to six days later, cells on the periphery of the sphere increased expression of biochemical markers for cardiomyocytes (α-sarcomeric actin, α-Sarc Act; d), smooth muscle (Smooth Muscle Actin, SMA; e), and endothelial (von Willebrand factor, vWF; f) cells (all shown in grey fluorescence). (F) Immunofluorescent staining shows that c-kit$^{pos}$ porcine CSCs have IGF-1 and HGF receptors (grey, Igf-1R and c-met, respectively). (G-H) When grown in culture, freshly isolated porcine c-kit$^{pos}$ cardiac cells respond to the stimulation of IGF-1 and HGF, by cell proliferation (G; *p<0.05 vs. base, †p<0.05 vs. CTRL, ‡p<0.05 vs. HGF) and migration (H; †p<0.05 vs. CTRL, ‡p<0.05 vs. IGF-1). (I) Western blot analysis revealed that upon ligand binding specific downstream effector pathways are activated in c-kit$^{pos}$ porcine cardiac cells. phos=phosphorylated, FAK=focal adhesion kinase.

FIG. 3 Intra-Coronary Injection of IGF-1 and HGF Improves Myocardial Cell Remodeling after AMI.

(A) H&E staining of GF-treated pig hearts revealed islands of survived myocardial tissue in the infarct zone (arrows), disposed between the regenerating and fibrotic layers. (B) These myocardial islands were infrequent and less defined in structure in the saline-treated CTRL pig hearts. (C) These myocardial islands were composed of mainly BrdU negative cardiomyocytes (cardiac troponin I, cTnI; grey with their nuclei as black circles in the middle of the cell), documenting their survived and mature phenotype. The cells born after the infarct are BrdU positive and their nuclei show as white dots. (D-E) Sirius red staining identified fibrotic tissue (grey staining) and muscle (yellow staining) in cross sections of the infarct zone, in GF-treated (D) and saline-treated CTRL (E) pig hearts. (F) GF-treated (IGF-1/HGF) pig hearts had a decreased percentage area fraction of fibrosis in the infarct zone, compared to saline-treated CTRL pigs. *$p<0.05$ vs. CTRL. †$p<0.05$ vs. IGF-1/HGF 1×. (G) Staining for activated caspase-3 (brown; arrowheads) revealed apoptotic myocytes in the peri-infarct/border zone of the CTRL pig heart after AMI. (H) IGF-1 and HGF injection resulted in decreased numbers of apoptotic myocytes, in the peri-infarct/border zone, compared to saline-treated CTRL. *$p<0.05$, vs. CTRL, †$p<0.05$ vs. IGF-1/HGF 1×, ‡$p<0.05$ vs. IGF-1/HGF 2×. (I) Analysis of myocyte diameter showed that GF-treated pigs had a decreased myocyte hypertrophic response after AMI, when compared to saline treated CTRL animals. Normal=remote/distal region from infarcted area in CTRL hearts. A$p<0.05$ vs. Normal, *$p<0.05$ vs. CTRL. †$p<0.05$ vs. IGF-1/HGF 1×.

FIG. 4 IGF-1 and HGF Administration after AMI Activates Endogenous CSCs, Driving their Commitment to the Cardiac Lineage (A-B) The majority of porcine ckit$^{pos}$ CSCs (white) express Igf-1 (A, grey) and c-met (B, grey) receptors in vivo. DAPI stains the nuclei in blue. (C) A cluster of ckit$^{pos}$ CSCs (white) in the area of infarct of a GF-4× treated pig heart. (D) The number of c-kit$^{pos}$ CSCs significantly increased in the border but more in the infarcted region of GF-treated pigs, compared to saline-treated CTRL. *$p<0.05$, vs. CTRL, †$p<0.05$ vs. IGF-1/HGF 1×, ‡$p<0.05$ vs. IGF-1/HGF 2×. (E) Many c-kit$^{pos}$ CSCs (white) in the GF-treated pig hearts were positive for BrdU (grey), indicative of their newly formed status. (F) c-kit$^{pos}$ CSCs (white) expressed the cardiac transcription factor, NRx2.5 (grey), representing cardiac progenitor cells. Nuclei were stained with DAPI (blue). (G) The number of c-kit$^{pos}$NRx2.5$^{pos}$ cardiac progenitor cells increased in the infarct and border zones in GF-treated pig hearts, *$p<0.05$, vs. CTRL, †$p<0.05$ vs. IGF-1/HGF 1×, ‡$p<0.05$ vs. IGF-1/HGF 2×. (H-I) Some c-kit$^{pos}$ CSCs (white) expressed the transcription factors, GATA6 (H; grey) and Ets-1 (I; grey), indicative of smooth muscle and endothelial cell differentiation, respectively.

FIG. 5. IGF-1/HGF Intracoronary Administration Induces Substantial New Myocyte Formation after AMI.

(A-B) Regenerating bands of small, newly formed BrdU$^{pos}$ (white) myocytes (grey; α-sarcomeric actin, α-Sarc Act) in the infarct regions of GF-1× (A) and GF-4× (B) treated pig hearts. Note the increased size of the regenerating band after 4× the amount of GF administration. Also the myocytes are more dense, compact and structured as myocardium after 4× the amount of GF administration. (C) Within these regenerating bands in the infarct zone were small Ki67$^{pos}$ (white) proliferating myocytes (grey; α-Sarc Act). (D-E) Newly formed small BrdU$^{pos}$ (white nuclei) myocytes (grey; α-Sarc Act cytoplasm) in the border zone after GF-1× (D) and GF-4× (E) doses. (F) Small Ki67$^{pos}$ (white) myocytes (grey; α-Sarc Act) were also present in the border zone after GF-injection. (G-H) The fraction of small BrdU$^{pos}$ and Ki67$^{pos}$ myocytes significantly increased in the border but more in the infarct region after GF injection. *$p<0.05$, vs. CTRL, †$p<0.05$ vs. IGF-1/HGF 1×, ‡$p<0.05$ vs. IGF-1/HGF 2×. (I) A small Ki67$^{pos}$ mitotic myocyte in the infarct zone of a GF-4× treated pig heart.

FIG. 6 Growth Factor Administration Increased the Generation of New Vascular Structures and Improved Cardiac Function in the Infarcted Pig Heart.

(A) Newly formed arterial structures (BrdU, white; α-smooth muscle actin, SMA, white; Myosin Heavy Chain, MHC, grey; DAPI, blue) were evident in the infarcted region of GF-treated pig hearts. (B-C) Newly formed capillaries were also evident in the infarcted regions after IGF-1 and HGF injection (BrdU, white; vWF, grey; DAPI, dark grey). (D-F) The number of capillaries in GF-treated pigs was significantly increased in the infarct zone, compared to saline treated (dark grey stain) CTRL. *$p<0.05$ vs. CTRL, †$p<0.05$ vs. IGF-1/HGF 1×, ‡$p<0.05$ vs. IGF-1/HGF 2×. Images (20× magnification) show vWF staining (dark grey) in saline-treated CTRL (D) and GF-4× (E) treated hearts. Capillaries were defined as vessels composed of 1 or 2 endothelial cells. (G-H) GF-treated hearts showed improved left ventricular (LV) ejection fraction (G) and radial strain (H), compared to saline-treated CTRL. *$p<0.05$ vs. Baseline, #$p<0.05$ vs. AMI, †$p<0.05$ vs. CTRL, ‡$p<0.05$ vs. GF-1×. (I) Representative Tissue Doppler radial strain tracing from CTRL (a-c) and GF-4× (d-f) treated pigs. CTRL (b) and GF-4× (e) treated pigs had equal de-synchronization of antero-septal contraction following 90 minutes of coronary occlusion (AMI). At sacrifice (Post-MI), de-synchronized contraction worsened in CTRL (c) while it was improved in GF-treated (f) pigs.

The results shown above demonstrate that microgram doses of these growth factors improve myocardial remodeling, foster the activation of the resident CSCs, which produce extensive new myocardial formation, improving LV function in a dose dependent manner in an animal heart of size and anatomy similar to the human using a clinically implementable protocol. Thus, IGF-1/HGF injection produced a wide variety of beneficial effects on cardiac remodeling and autologous cell regeneration that were proportional to the dose of GF administered.

Figure 7:
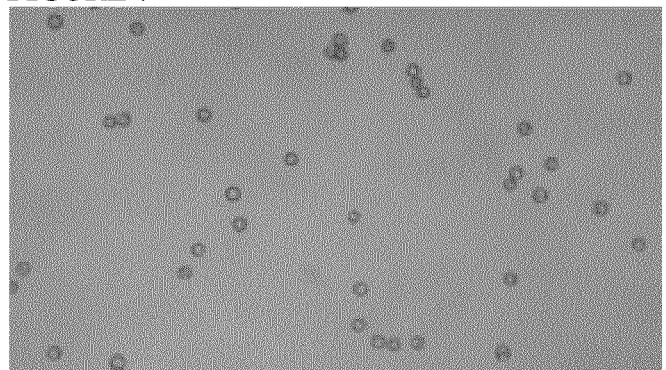
FIG. 7 shows an optical microscope image of PLGA particles with IGF-1 prepared as per Example 1.

FIG. 7 shows Optical microscope image of the PLGA particles containing IGF-1 obtained with the recipe described above FIG. 8 shows an electron micrograph of the same batch of particles shown in the figure above.

Figure 9:
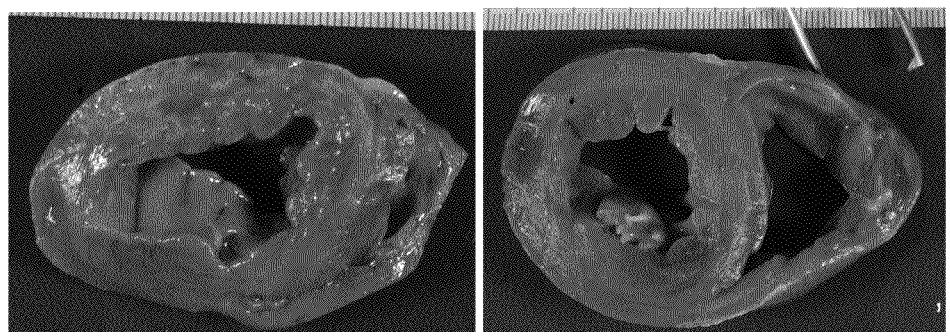
FIG. 9 shows sections of porcine heart.

FIG. 9 shows sections of the hearts of pig #1 (left image) and pig #2 (right image). The anterior wall of the left ventricle, irrigated by the left coronary artery, of pig #1 shows a number of microinfarcts (paler areas), while the myocardium of pig #2 is normal as shown by the uniform coloration.

Figure 10A:
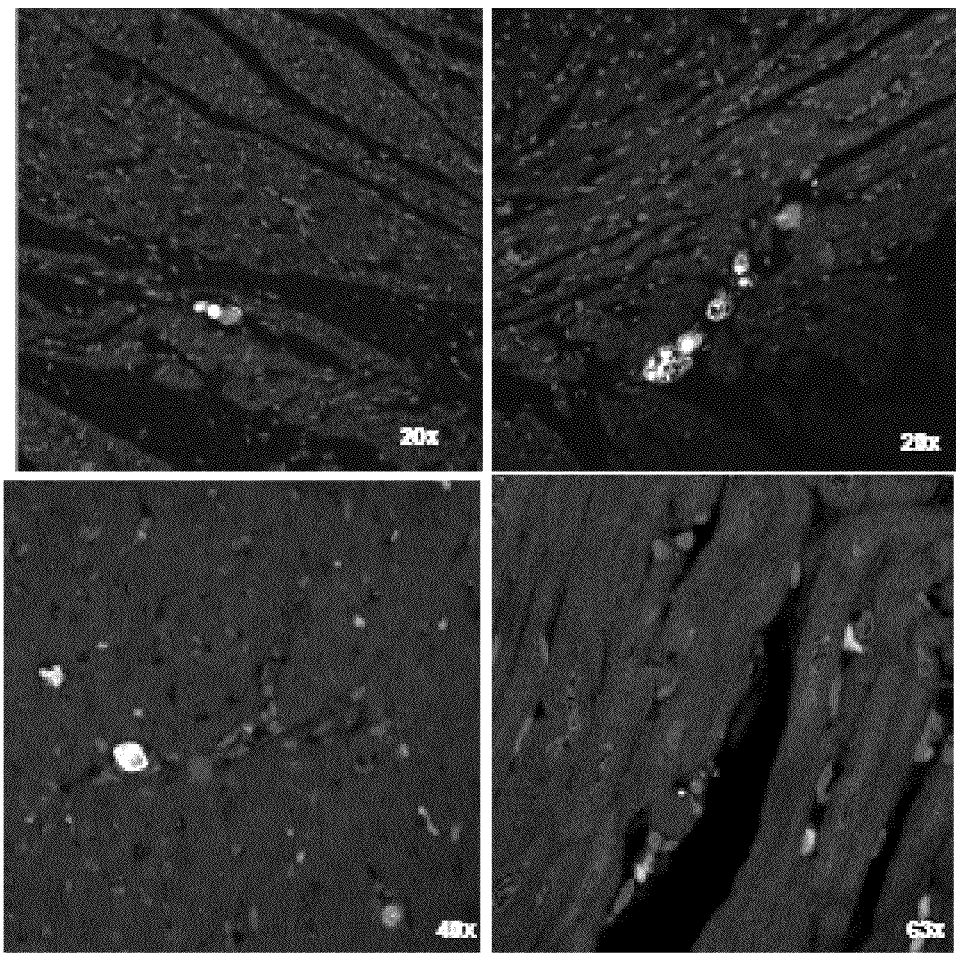
FIGS. 10A-10C are micrographs and show sections of porcine myocardium after administration of polystyrene microspheres or PLGA and growth factor microspheres.
Figure 10B:
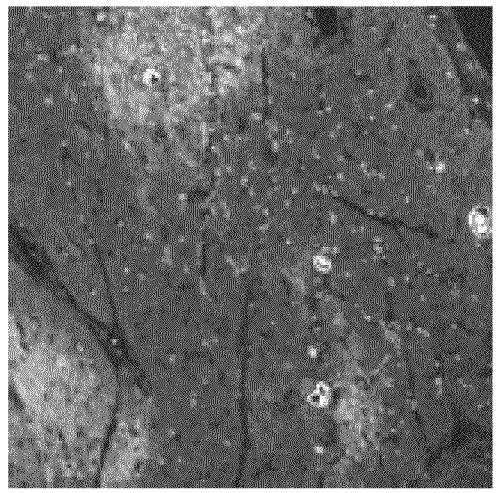
Figure 10B:
Figure 10B:
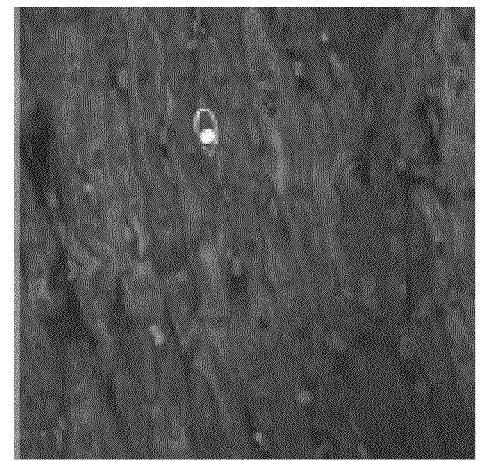
Figure 10C:
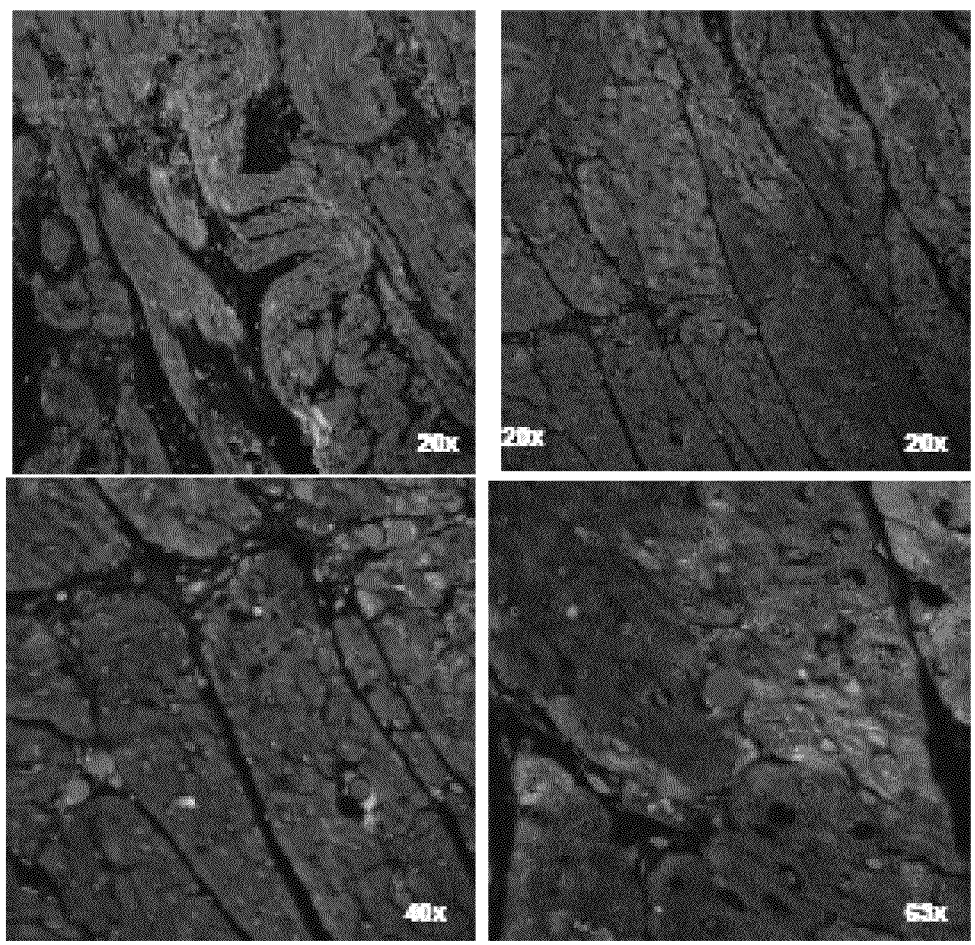

FIG. 10A. Sections of the myocardium of pig #3, sacrificed 30 min after the administration of a mixture of polystyrene (red beads-shown in the figure as grey, larger diameter, smooth circles) and PLGA+growth factors (green beads-shown in the figure as white, smaller diamter and more irregular shape) beads. The apperence difference in size between the red and green particles is due to the higher fluorescence of the red FIGS. 10B and 10C show sections of the myocardium of pig #4, sacrificed 24 hours after the administration of a mixture of polystyrene (red—shown in figures as grey, larger diameter, smooth circles) and PLGA+growth factors (green—shown in the figure as white, smaller diamter and more irregular shape) beads. The ratio of green to red beads is significantlo lower in this animal because of the degradation of the PLGA microparticles In the four panel of the left only red beads are detected, while in those of the right the ratio is closer to 1:1.

FIG. 11 shows Microscopic sections of two areas of pig #4. Myocytes are in grey. Nuclei in darker grey. The endogenous cardiac stem cells (CSCs) are identified by an arrow head (upper) and an arrow (lower). Their membrane is labeled in paler green. On the upper figure, the nuclei are clean because the cells are quiescent. On the lower figure all the CSCs have pale grey stain in the nuclei that identifies the protein Ki-67 a marker of cells that have entered the cell cycle.

FIG. 12. Local Administration of IGF-1 and HGF Encapsulated into 15 μm PLGA Microspheres Enhances the Regeneration of Damaged Skeletal Muscle.

Histological images of control and damaged quadriceps muscle. Panel A: Histological image of the left muscle (control) five days after producing the lesion on the right muscle. No treatment was administered to this leg. Panel B: Histological section of a right quadriceps five days after producing the damage with no treatment (damaged control). The arrowheads point to two of the several extensive areas of cell necrosis where a concentration of nuclei appear to initiate a regenerative reaction. Panel C: Right biopsy of right quadriceps 3 days after the lesion treated with a mixture of microspheres loaded with IGF-1 and microspheres loaded with HGF with a total administered equivalent of 16 μg IGF-1 and 4 μg HGF. The arrow heads point toward young microfibers in the damaged areas in a very process of regeneration. Panel D: Biopsy of the same muscle shown in Panel C two days later (5 days after the lesion). The smaller sized dark fibers are regenerated fibers labeled with an antibody against embryonic myosin heavy chain, a marker or regenerated fibers. The image in this panel is the equivalent to the one in Panel B. The striking difference between the two images shows the effectiveness of the therapy.

FIG. 13. Enhanced Myocardial Regenerative Capacity of the Combination of IGF-1/HGF/SCF Administered Intracoronary Encapsulated in PLGA Microspheres of 15 μm in Diameter The bar graph of FIG. 13A compares the effect in the number of regenerated cardiac myocytes in pigs post-AMI treated with a combination of two types of microspheres, white bars (one loaded with IGF-1 and the other with HGF) with the animals treated with a combination of three types of microspheres (hrIGF-1, hrHGF, and hrSCF), black bars. It is obvious that at the three different concentrations used the combination of 3 types of microspheres each loaded with a different factor is superior to the combination of only two. CTRL=control animals treated with placebo; White bars: 1× animals administered microspheres loaded with the equivalent of 2 μg IGF-1 and 0.5 μg HGF biologically active; 2X=4 μg IGF-1 and 1 μg HGF and 4× dose=8 μg of IGF-1 and 2 μg of HGF. Black bars: Same amounts of IGF-1 and HGF as for the animals represented by the white bars plus microspheres loaded with SCF equivalent to 2, 4 and 8 μg of biologically active hrSCF FIG. 13B shows the left ventricle ejection fraction prior to, immediately after and 4 weeks post-AMI as determined by echocardiography of the pigs treated with different combinations of microspheres. Baseline=LV ejection fraction just prior the AMI; AMI=LV ejection fraction after AMI; Post-AMI=LV ejection fraction 4 weeks after AMI and local GF treatment. C=Control animals treated with placebo post-AMI; ○=animals treated with 4× dose of IGF-1+HGF in solution intracoronary; ▼=animals treated with a 4× dose of IGF-1+HGF encapsulated in PLGA microspheres administered just downstream to the site of coronary occlusion; Δ=animals treated with a 4× dose of IGF-1+HGF+SCF each separately encapsulated in PLGA microspheres administered just downstream to the site of coronary occlusion.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

Embodiments of the disclosure are hereby described as comprising integers. The disclosure also extends to separate embodiments consisting of or consisting essentially of said integers.

It is also specifically envisages that the disclosure extends to combinations of one or more embodiments described herein, where technically feasible.

All patents and patent applications referred to herein are incorporated by reference in their entirety.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims.

The invention claimed is:

1. A pharmaceutical formulation for parenteral administration to a target tissue comprising particles containing an active ingredient and a biodegradable excipient: wherein the mean diameter of the particles is 15 microns and 99% or more of the particles have a diameter of 15±1 microns,
wherein the diameter of 15±1 microns confers upon the particles retention in a target tissue following administration of the pharmaceutical formulation upstream of the target tissue;
and wherein the formulation is substantially free of particles with a diameter greater than 50 microns and less than 5 microns, and wherein the active ingredient comprises a growth factor selected from the group consisting of: HGF (hepatocyte growth factor); IGF (insulin-like growth factor); PDGF (Platelet-derived growth factor); FGF (fibroblast growth factor); SDF-1 (stromal cell-derived factor 1); EGF (epidermal growth factor); VEGF (vascular endothelial growth factor); erythropoietin (EPO); TGF β (transforming growth factor β); G-CSF (Granulocyte-colony stimulating factor); GM-CSF (Granulocyte-macrophage colony stimulating factor), Bone morphogenetic proteins (BMPs); Activin A; IL-6; Neurotrophins; TPO (Thrombopoietin); GDF-8 (Myostatin); GDF9 (Growth differentiation factor-9); Periostin, Wint 3A, Neuroregulin, SCF-1 and combinations thereof.

2. A pharmaceutical formulation according to claim 1, which is substantially free of particles with a diameter greater than 20 microns and less than 5 microns.

3. A pharmaceutical composition according to claim 1 wherein the active ingredient is selected from the group consisting of HGF, IGF and combinations thereof.

4. A pharmaceutical composition according to claim 3 which further comprises PDGF (Platelet-derived growth factor), FGF (fibroblast growth factor); SDF-1 (stromal cell-derived factor 1); EGF (epidermal growth factor); VEGF (vascular endothelial growth factor); erythropoietin (EPO); TGF β (transforming growth factor β); G-CSF (Granulocyte-colony stimulating factor); GM-CSF (Granulocyte-macrophage colony stimulating factor); Bone morphogenetic proteins (BMPs); Activin A; IL-6; Neurotrophins; TPO (Thrombopoietin); GDF-8 (Myostatin); GDF9 (Growth differentiation factor-9); Periostin, Wint 3A or Neuroregulin.

5. A pharmaceutical composition according to claim 4 which further comprises stem cell factor-1 (SCF-1).

6. A pharmaceutical composition according to claim 1, wherein the concentration of the active ingredient is in the range of 1 ng per $1 \times 10^6$ particles up to 4 mg per $1 \times 10^6$ particles.

7. A pharmaceutical formulation according to claim 1, wherein at least 30% of the active ingredient is retained in the target tissue after administration.

8. A pharmaceutical formulation according to claim 7, wherein at least 40%, at least 50%, at least 60%, at least 70%, or at least 80% of the active ingredient is retained.

9. A pharmaceutical composition according to claim 1, wherein the parenteral administration is intra-arterial administration.

10. A pharmaceutical composition according to claim 1 wherein the pharmaceutical composition comprises a mixed population of particles, said population comprising particles containing a first active ingredient selected from HGF and/or IGF in admixture with particles containing one or more further active ingredients.

11. A pharmaceutical composition according to claim 10 wherein the one or more further active ingredients is/are selected from the group consisting of PDGF (Platelet-derived growth factor); FGF (fibroblast growth factor); SDF-1 (stromal cell-derived factor 1); EGF (epidermal growth factor); VEGF (vascular endothelial growth factor); erythropoietin (EPO); TGF β (transforming growth factor β); G-CSF (Granulocyte-colony stimulating factor); GM-CSF (Granulocyte-macrophage colony stimulating factor), Bone morphogenetic proteins (BMPs); Activin A; IL-6; Neurotrophins; TPO (Thrombopoietin); GDF-8 (Myostatin); GDF9 (Growth differentiation factor-9); Periostin, Wint 3A, Neuroregulin, SCF-1 and combinations thereof.

12. A pharmaceutical composition according to claim 11, wherein the one or more further active ingredients is/are selected from the group consisting of active ingredient comprises a growth factor selected from the group consisting of IGF-1; PDGF-β, aFGF (FGF-1), bFGF (FGF-2), FGF-4, BMP-2, BMP-4, NGF (Nerve growth factor), BDNF (brain-derived neurotrophic factor), NT-3 (neurotrophin-3), NT-4 (neurotrophin-4) and NT-1 (neurotrophin-1); or a combination thereof.

13. A pharmaceutical composition according to claim 1 wherein the active ingredient is selected from the group consisting of IGF-1; PDGF-β, aFGF (FGF-1), bFGF (FGF-2), FGF-4, BMP-2, BMP-4, NGF (Nerve growth factor), BDNF (brain-derived neurotrophic factor), NT-3 (neurotrophin-3), NT-4 (neurotrophin-4) and NT-1 (neurotrophin-1); or a combination thereof.

14. A pharmaceutical composition according to claim 4, wherein the further active ingredient is selected from the group consisting of PDGF-β, aFGF (FGF-1), bFGF (FGF-2), FGF-4, BMP-2, BMP-4, NGF (Nerve growth factor), BDNF (brain-derived neurotrophic factor), NT-3 (neurotrophin-3), NT-4 (neurotrophin-4) and NT-1 (neurotrophin-1); or a combination thereof.

15. A method of localized delivery comprising the step of administering into the circulation upstream of cardiac tissue a pharmaceutical composition as defined in claim 1.

16. A method according to claim 15 wherein the localized delivery is through intra-arterial administration.

17. A method for the treatment of myocardial infarction, acute or chronic ischemic heart disease, with or without a myocardial infarction or cerebral vascular accident (stroke), the method comprising administering to the coronary artery of a patient in need of such treatment a suitable amount of a pharmaceutical composition according to claim 1.

18. A method for the treatment of myocardial infarction, acute or chronic ischemic heart disease, with or without a myocardial infarction or cerebral vascular accident (stroke), the method comprising administering to the coronary artery of a patient in need of such treatment a suitable amount of a pharmaceutical composition according to claim 10.

19. A method for the treatment of cell loss produced as a consequence of reduced blood flow (ischemia), the method comprising administering to the coronary artery of a patient in need of such treatment a suitable amount of a pharmaceutical composition according to claim 1.

20. A method for the treatment of cell loss produced as a consequence of reduced blood flow (ischemia), the method comprising administering to the coronary artery of a patient in need of such treatment a suitable amount of a pharmaceutical composition according to claim 10.

21. A pharmaceutical composition according to claim 1 wherein the active ingredient is selected from the group consisting of HGF, IGF, and stem cell factor-1 (SCF-1); or a combination thereof.

* * * * *